(12) United States Patent
Hellman

(10) Patent No.: US 6,913,749 B2
(45) Date of Patent: Jul. 5, 2005

(54) IMMUNOGENIC POLYPEPTIDES FOR INDUCING ANTI-SELF IGE RESPONSES

(75) Inventor: Lars T. Hellman, Uppsala (SE)

(73) Assignee: Resistentia Pharmaceuticals AB (SE)

( * ) Notice: Subject to any disclaimer, the term of this patent is extended or adjusted under 35 U.S.C. 154(b) by 0 days.

(21) Appl. No.: 09/401,636

(22) Filed: Sep. 22, 1999

(65) Prior Publication Data

US 2001/0038843 A1 Nov. 8, 2001

Related U.S. Application Data

(60) Provisional application No. 60/106,652, filed on Nov. 2, 1998.

(51) Int. Cl.$^7$ .................. A61K 39/00; A61K 39/395; C07K 16/46
(52) U.S. Cl. .................. 424/185.1; 424/192.1; 530/387.3
(58) Field of Search .................. 424/185.1, 192.1; 530/387.3

(56) References Cited

U.S. PATENT DOCUMENTS

| 4,483,793 A | 11/1984 | Vyas |
| 4,683,195 A | 7/1987 | Mullis et al. |
| 4,703,004 A | 10/1987 | Hopp et al. |
| 4,767,842 A | 8/1988 | Stevens |
| 4,782,137 A | 11/1988 | Hopp et al. |
| 4,873,191 A | 10/1989 | Wagner et al. |
| 5,175,384 A | 12/1992 | Krimpenfort et al. |
| 5,175,385 A | 12/1992 | Wagner et al. |
| 5,196,197 A | 3/1993 | Talwar et al. |
| 5,254,671 A | * 10/1993 | Chang |
| 5,501,855 A | 3/1996 | Talwar et al. |
| 5,580,859 A | 12/1996 | Felgner et al. |
| 5,589,466 A | 12/1996 | Felgner et al. |
| 5,653,980 A | * 8/1997 | Hellman et al. |
| 5,698,201 A | 12/1997 | Stevens |
| 5,733,553 A | 3/1998 | Talwar et al. |
| 5,762,931 A | 6/1998 | Talwar et al. |
| 5,827,668 A | 10/1998 | Stanworth et al. |
| 5,837,686 A | 11/1998 | Kirby et al. |
| 5,945,104 A | 8/1999 | Stanworth et al. |
| 5,955,076 A | 9/1999 | Stanworth et al. |
| 6,034,066 A | 3/2000 | Johnson et al. |
| 2002/0141989 | 10/2002 | Kricek et al. |

FOREIGN PATENT DOCUMENTS

| CA | 2117193 | 4/1993 |
| CA | 2320960 | 2/1999 |
| EP | 0 327 378 | 8/1989 |
| EP | 0 396 505 | 11/1990 |
| EP | 0 403 312 | 12/1990 |
| EP | 0 752 886 B1 | 1/1998 |
| EP | 0 841 946 B1 | 10/2002 |
| EP | 1 009 382 | 6/2003 |
| EP | 0 821 003 | 8/2003 |
| WO | WO 89/04834 | 6/1989 |
| WO | WO 89/06138 | 7/1989 |
| WO | WO 91/01146 | 2/1991 |
| WO | WO 91/11456 | 8/1991 |
| WO | WO 94/05698 | 3/1994 |
| WO | WO 94/08601 | 4/1994 |
| WO | WO 95/05849 | * 3/1995 |
| WO | WO9526356 | * 10/1995 |
| WO | WO 95/26365 | 10/1995 |
| WO | WO 96/12740 | 5/1996 |
| WO | WO 97/22699 | 6/1997 |
| WO | WO 98/05684 | 2/1998 |
| WO | WO 98/46642 | 10/1998 |
| WO | WO 99/62550 | 12/1999 |
| WO | WO 99/67293 | 12/1999 |
| WO | WO 00/20027 | 4/2000 |
| WO | WO 00/32227 | 6/2000 |
| WO | WO 00/65058 | 11/2000 |
| WO | WO 02/09751 | 2/2002 |
| WO | WO 02/20038 | 3/2002 |
| WO | WO02/102320 | 12/2002 |

OTHER PUBLICATIONS

Attwood et al, The Babel of Bioinformatics, 2000 Science vol. 290 No. 5491: 471–473.*
Nissim et al, EMBO J 10(1): 101–107, 1991.*
Ngo et al, 1994, The Protein Folding Problem and Tertiary Structure Prediction, pp. 492–495.*
Nissim et al. Comp. to Meth. Enzmol., p. 124–131, 1995.*
Nechansky et al, Int Arch Allergy Immunol. Dec., 1999;120(4):295–302.*
Abaza et al, J of Protein Chemistry 11(5): 433–444, 1992.*
Kuby et al., 1994, Immunology, second etition, pp. 85–96.*
Stryer et al, in Biochemistry, Third edition, W H Freeman Company, New York, pp. 31–33, 1998.*
Aveskogh et al, Eur J Immunol 28(9): 2738–50.*
Jaffery et al, Immunology 78(4): 635–42, Apr. 1993.*
Demoly et al, Am J Respir Crit Care Med 156(5): 1707, Nov. 1997.*

(Continued)

*Primary Examiner*—Christina Chan
*Assistant Examiner*—Phuong Huynh
(74) *Attorney, Agent, or Firm*—Fish & Richardson P.C., P.A.

(57) ABSTRACT

The invention relates to methods and materials involved in the treatment and prevention of various diseases such as infections and IgE-related diseases. Specifically, the invention relates to methods and materials that can be used to vaccinate a mammal against specific self or non-self antigens. For example, the methods and materials described herein can be used to reduce the effects of IgE antibodies within a mammal by reducing the amount of total and receptor bound IgE antibodies in the mammal. In addition, the invention provides vaccine conjugates, immunogenic polypeptides, nucleic acid molecules that encode immunogenic polypeptides, host cells containing the nucleic acid molecules that encode immunogenic polypeptides, and methods for making vaccine conjugates and immunogenic polypeptides as well as nucleic acid molecules that encode immunogenic polypeptides. Further, the invention provides an IgE vaccine that induces an anti-self IgE response in a mammal.

3 Claims, 11 Drawing Sheets

OTHER PUBLICATIONS

Figure 3A:
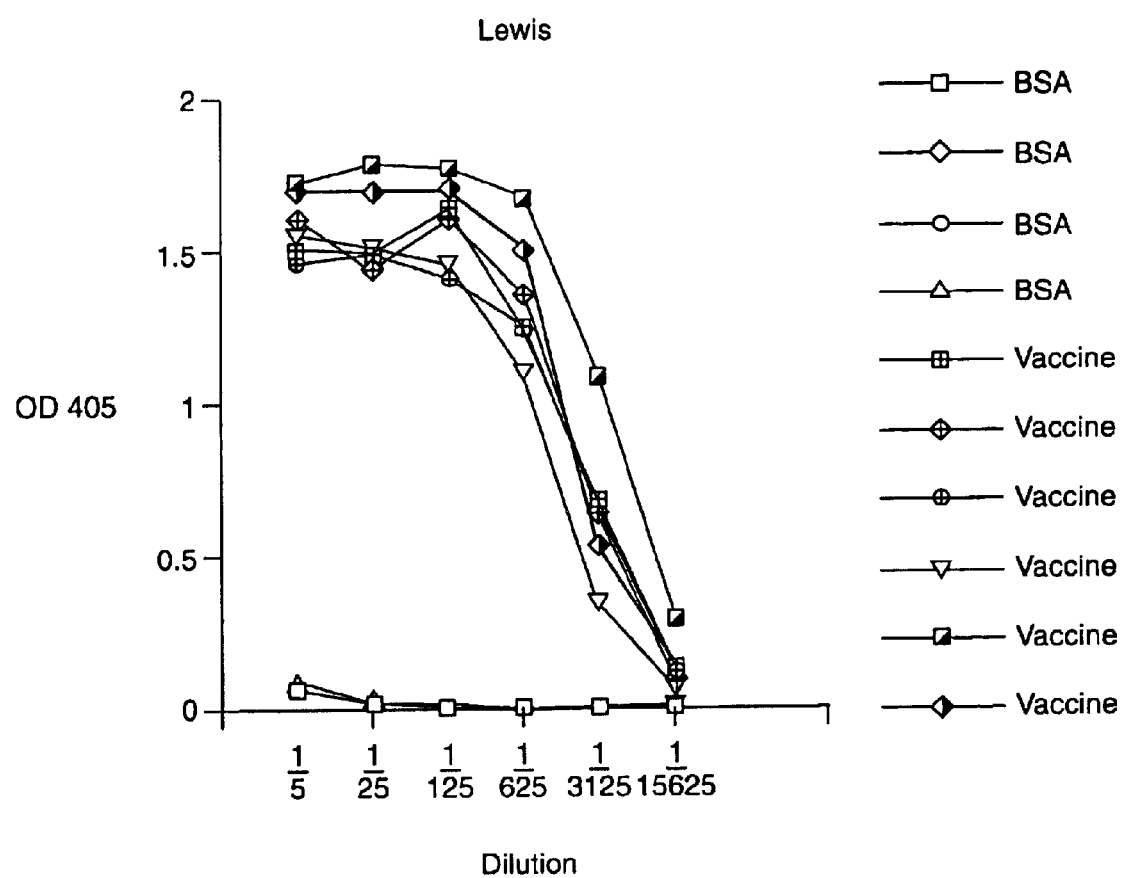

Keegan et al, Mol Immunol 28(10): 1149–54, Oct. 1991.*
Presta et al, J Biol Chem 269(42): 26368–73, Oct. 1994.*
Basu et al, J Biol Chem 269 268(18): 13118–13127, 1993.*
Hellman et al, in New Horizons in Allergy Immunotherapy, Plenum Press, New York, 1996, pp. 337–342.*
Paul et al (in Fundamental Immunology second edition, p. 826, Raven Press, New York, 1989.*
Fahy et al, Am J Respir Crit Care Med 155(6): 1824–34, Jun. 1997.*
Demoly and Bousquet, "Anti–IgE Therapy for Asthma," *Am. J. Respir. Crit. Care. Med.*, 1997, 155:1825–1827 (Erratum, only).
Fahy et al., "The Effect of an Anti–IgE Monoclonal Antibody on the Early– and Late–Phase Responses to Allergen Inhalation in Asthmatic Subjects," *Am. J. Respir. Crit. Care Med.*, 1997. 155:1828–1834.
Jaffery et al., "Induction of an auto–anti–IgE response in rats. IV. Effects on mast cell degranulation." *Immunology*, 1993, 78:635–642.
Nechansky et al., "Interaction of Human IgE with Fc Epsilon RI Alpha Exposes Hidden Epitopes on IgE," *Int. Arch. Allergy Immunol.*, 1999, 120:295–302.
Paul (ed.), *Fundamental Immunology*, 2$^{nd}$ edition, 1989, Raven Press, New York, pp. 826–827.
Basu et al., "Purification and characterization of human recombinant IgE–Fc fragments that bind to the human high affinity IgE receptor," *J. Biol. Chem.*, 1993, 268(18):13118–13127.
Nissum et al., "Fine Specificity of the IgE Interaction with the Low and High Affinity Fc Receptor," *J. Immunol.*, 1993, 150(4):1365–1374.
Liou et al., *J. Immunol.*, 143:3967–3975 (1989).*
Baniyash, et al., *Molecular Immunology*, 1988, 25(8):705–711.
Basciano, et al., *J. of Biol. Chem.*, 1986, 261(25):11823–11831.
Burt, et al., *Eur. J. Immunol.*, 1987, 17:437–440.
Burt, et al., *Molecular Immunology*, 1986, 23(2):181–191.
Coleman, et al., *Eur. J. Immunol.*, 1985, 15:966–969.
Geha, *Annals of Allergy*, 1991, Letter to the Editor, 66(5):359–360.
Geha, et al., *Nature*, 1985, 315:577–581.
Gould, *Clinical and Experimental Allergy*, 1991, 21, Supp. 1.
Haba, et al., *Journal of Immunological Methods*, 1987, 105:193–199.
Haba, et al., *Proc. Natl. Acad. Sci.*, 1987, 84:5009–5013.
Haba, et al., *Proc. Natl. Acad. Sci.*, 1990, 87:3363–3367.
Hamburger, *American Scientist*, 1976, 64:157–164.
Hamburger, *Annals of Allergy*, Letter to the Editor, Jan. 1992, 68(1).
Hamburger, *Science*, 1975, 189:389–390.
Hamburger, *Immunology*, 1979, 38(4):781–787.
Hamburger, *IgE and Allergy*, 95–112.
Holgate, *The Practioner*, 1989, 233:599–602.
Ishizaka, *Advances in Immunology*, 1989, 47:1–43.
Ishizaka, et al., *Proc. Natl. Acad. Sci.*, 1986, 83:8323–8327.
Johansson, *Anti–IgE Antibodies in Human Serum*, *J. Allergy Clin. Immunol.*, 1986, 77(4):555–557.
Koike, et al., *Monogr Allergy*, 1989, 26:165–175.
Liou, et al., *Journal of Immunology*, 1989, 143:3967–3975.
Marshall, et al., *Eur. J. Immunol.*, 1985, 15:272–277.
Marshall, et al., *Eur. J. Immunol.*, 1987, 17:445–451.
Marshall, et al., *Immunology*, 1989, 66(3):428–433.
Michel, et al., *J. Allergy Clin. Immunol.*, 1986, 1022–1027.
Nagpal, et al., *Journal of Immunology*, 1989, 142(10):3411–3415.
Neuberger, et al., *Nature*, 1985, 314(21):268–270.
Noro, et al., *Journal of Immunology*, 1986, 137(4):1258–1263.
Padlan, et al., *Molecular Immunology*, 1986, 23(10):1063–1075.
Robertson, et al., *Molecular Immunology*, 1988, 25(2):103–113.
Sarfati, et al., *Eur. J. Immunol.*, 1986, 16:325–331.
Slater, et al., *Journal of Immunology*, 1988, 140:807–811.
Stanworth, *Use of Synthetic Peptides in the Delineation of the Role of Non–Antigen Receptors in Mast Cell Signalling Processes*, 213–222.
Stanworth, et al., *Molecular Immunology*, 1984, 21(12):1183–1190.
Stanworth, et al., *The Use of Synthetic Peptides in the Delineation of Immunoglobulin Antigenic Epitopes and Fc Effector Functions*, 226–244.
Stanworth, et al., *Biochem. J.*, 1979, 180:665–668.
Suemura, et al., *Journal of Immunology*, 1986, 137(4):1214–1220.
Weyer, et al., *Agents and Actions*, 1987, 20, ¾:210–212.
Weyer, et al., *Agents and Actions*, 1987, 20 ¾:206–209.
Vichyanond, *Asian Pacific Journal of Allergy and Immunology*, 1990, 8:1–4.
Chemical Abstracts, vol. 129 (Columbus, Ohio), Griot–Wenk, M. E. et al., "Characterization of two dog IgE–specific antibodies elicited by different recombinant fragments of the epsilon chain in hens," p. 1, Abstract No. 107756, Vet. Immunol. Immunopathol. 1998, 64(1): Abstract.
Chemical Abstracts, vol. 128 (1999), (Columbus, Ohio, USA), Rudolf, Michael P. et al., "Epitope–specific antibody response to IgE by mimotope," p. 1, Abstract No. 320498, J. Immunol., 1998, 160(7): Abstract.
Dialog Information Services, file 155, MEDLINE, Dialog accession No. 07797491, Medline accession No. 93293823, Basu M. et al., "Purification and characterization of human recombinant IgE–Fc IgE receptor," J. Biol. Chem., Jun. 25, 1993, 268(18): Abstract.
Dialog Information Services, file 155, MEDLINE, Dialog accession No. 05892828, Medline accession No. 89212964, Glovksy MM et al., "Effect of monoclonal antihuman IgE on recombinant IgE (301–376) inhibition of specific IgE histamine release," Int. Arch. Allergy Appl. Immunol., 1989, 88(1–2): Abstract.
XVIth International congress of allergology and clinical immunology, Oct. 1997, Beda M. Stadler et al., "Anti–IgE Vaccination," pp. 339–343, see p. 341, left column.
Abaza et al., *J. Protein Chem.*, 1992, 11(5):433–444.
Aveskogh et al., *Eur. J. Immunol.*, 1998, 28:2738–2750.
Baniyash et al., *Eur. J. Immunol.*, 1984, 14:799–807.
Barouch et al., *J. Immunol.*, 1998, 161(4):1875–1882.
Burt et al., *Mol. Immunol.*, 1987, 24(4):379–389.
Dalum et al., *J. Immunol.*, 1996, 157(11):4796–4804.
Dalum et al., *Mol. Immunol.*, 1997, 34(16–17):1113–1120.
Devlin, Ph.D. (editor), *Textbook of Biochemistry*, 2$^{nd}$ Edition, John Wiley & Sons, pp. 49–57.
Froese, *CRC Crit. Rev. Immunol.*, 1980, 1:79–132.
Gordon, *Intl. Rev. Cytol.*, 1989, 115:171–229.
Gossler et al., *Proc. Natl. Acad. Sci. USA*, 1986, 83:9065–9069.

Gould et al., *Int. Archs. Allergy Appl. Immun.*, 1987, 82:392–393.
Hammer et al., *Nature*, 1985, 315:680–683.
Hellman et al., *Nucleic Acids Res.*, 1982, 10:6041–6049.
Hellman, *Eur. J. Immunol.*, 1994, 24:415–420.
Helm et al., *Nature*, 1988, 331:180–183.
Helm et al., *Proc. Natl. Acad. Sci. USA*, 1989, 86:9465–9469.
Helm et al., *J. Biol. Chem.*, 1996, 271:7494–7500.
Helm et al., *Allergy*, 1997, 52:1155–1169.
Krimpenfort et al., *Bio/Technology*, 1991, 9:844–847.
Lowenadler et al., *Mol. Immunol.*, 1992, 29(10):1185–1190.
Maecker et al., *Vaccine*, 1997, 15(5):1687–1696.
Margolskee et al., *Mol. Cell Biol.*, 1988, 8:2837–2847.
Morein, *Vet. Microbiol.*, 1990, 23(1–4):79–84.
Palmiter et al., *Cell*, 1985, 41:343–345.
Pluckthun, *Biotechnology*, 1991, 9:545–551.
Presta et al., *J. Biol. Chem.*, 1994, 269:26368–26373.
Purscel et al., *Science*, 1986, 244:1281–1288.
Rammensee et al., *Immunogenics*, 1995, 41:178–228.
Rodriguez et al., *J. Gen. Virol.*, 1999, 80(Pt.1):217–223.
Schnieke et al., *Science*, 1997, 278:2130–2133.
Smith et al., *Gene*, 1988, 67(1):31–40.
Spiegelberg et al., *J. Clin. Lab. Analysis*, 1987, 1:251–261.
Stanworth et al., *Lancet*, 1990, 336(8726):1279–1281.
Thompson et al., *Cell*, 1989, 56:313–321.
Van der Putten et al., *Proc. Natl. Acad. Sci. USA*, 1985, 82:6148–6152.
Vercelli et al., *Nature*, 1989, 338(6217):649–651.

* cited by examiner

```
         10        20        30        40        50        60
1    D----NKTFSVCSRD---FTPPTVKILQSSCDGGGHFPPTIQLLCLVSGYTPGTINITW   Human IgE C2C3C4
1    DLTIRAR-------PVNITKPTVDLLHSSCDPNA-FHSTIQLYCFVYGHIQNDVSIHW   Rat IgE C2-C3-C4
1    EFHHHHHHTLSLPESGPVTIIPPTVKLFHSSCDPRGDAHSTIQLLCLVSGFSPAKVHVTW   His6-Op2-3-4

70        80        90       100       110       120
53   LEDGQVMD--VDLSTASTTQEGELASTQSELTLSQKHWLSDRTYTCQVTYQGHTFEDSTK   Human IgE C2C3C4
51   LMDDRKIYETHAQNVLIK-EEGKLASTYSRLNITQQWMSESTFTCKVTSQGENYWAHTR   Rat IgE C2-C3-C4
61   LVDGQEAENLFPYTTRPKREGGQTFSLQSEVNITQGQWMSSNTYTCHVKHNGSIFEDSAQ   His6-Op2-3-4

130       140       150       160       170       180
111  KCADSNPRGVSAYLSRPSPFDLFIRKSPTITCLVVDLAPSKGTVNLTWSRASGKPVNHST   Human IgE C2C3C4
110  RCSDDEPRGVITYLIPPSPLDLYENGTPKLTCLVLDLES-EENITVTWVRERKKSIGSAS   Rat IgE C2-C3-C4
121  KCSDTDPRGISAYILPPTPQDLFVKKVPTIGCLIVDLASAEN-VKVTWSRESGGPVNPSS   His6-Op2-3-4

190       200       210       220       230       240
171  RKEEKQRNGTLTVTSTLPVGTRDWIEGETYQCRVTHPHLPRALMRSTTKTSGPRAAPEVY   Human IgE C2C3C4
169  QRSTKHHNATTSITSILPVDAKDWIEGEGYQCRVDHPHFPKPIVRSITKAPGKRSAPEVY   Rat IgE C2-C3-C4
180  LVVKEQYNGTFTVTSHLPVNTDDWIEGDTYTCRLESPDMPVPLIRTISKAPGKRLAPEVY   His6-Op2-3-4

250       260       270       280       290       300
231  AFATPEWPGSRDKRTLACLIQNFMPEDISVQWLHNEVQLPDARHSTTQPRKTKGSG--FF   Human IgE C2C3C4
229  VFLPPE-EEEKDKRTLTCLIQNFFPEDISVQWLQDSKLIPKSQHSTTTPLKYNGSNQRFF   Rat IgE C2-C3-C4
240  MLP-PSPEETGTTRTVTCLIRGFYPSEISVQWLFNNEEDHTGHHTTRPQKDHGTDPSFF   His6-Op2-3-4

310       320       330       340       350
289  VFSRLEVTRAEWEQKDEFICRAVHEAASPSQTVQRAVSVNPGK                   Human IgE C2C3C4
288  IFSRLEVTKALWTQTKQFTCRVIHEALREPRKLERTISKSLGNTSLRPSQASM         Rat IgE C2-C3-C4
299  LYSRMLVNKSIWEKGNLVTCRVVHEALPGSRTLEKSLHYSAGN                   His6-Op2-3-4
```

*Fig. 1*

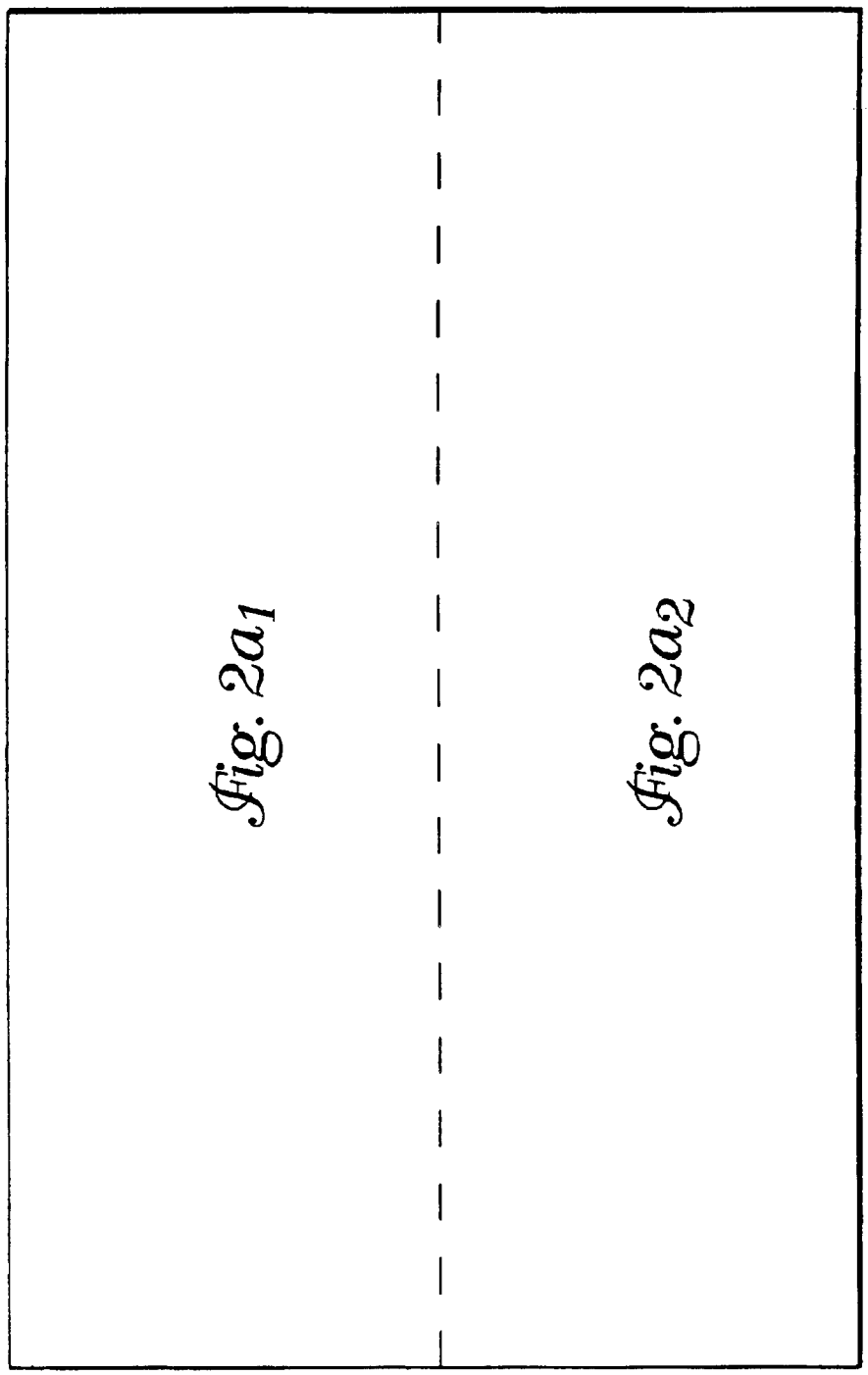
Fig. 2a₁  Fig. 2a₂  Fig. 2a

Fig. 2a₁

```
    1  EFHHHHHHTLSLPESGPVTIIPPTVKLFHSSCDPRGDAHSTIQLLCLVSGFSPAKVHVTW  His6-OpC2-RatC3-OpC4
    1  EFHHHHHHTLSLPESGPVTIIPPTVKLFHSSCDPRGDAHSTIQLLCLVSGFSPAKVHVTW  His6-Op2-ratOp3-Op4
    1  EFHHHHHHTLSLPESGPVTIIPPTVKLFHSSCDPRGDAHSTIQLLCLVSGFSPAKVHVTW  His6-Op2-Mouse3-Op4
    1  EFHHHHHHTLSLPESGPVTIIPPTVKLFHSSCDPRGDAHSTIQLLCLVSGFSPAKVHVTW  His6-Op2-3-4
    1  EFHHHHHHTEVYSDSSK-DPIPPTVKLLHSSCDPRGDSQASIELLCLITGYSPAGIQVDW  His6-Platypus C2-C3-C4

61  LVDGQEAENLFPYTTRPKREGGQTFSLQSEVNITQGQWMSSNTYTCHVKH--NGSIFEDS  His6-OpC2-RatC3-OpC4
   61  LVDGQEAENLFPYTTRPKREGGQTFSLQSEVNITQGQWMSSNTYTCHVKH--NGSIFEDS  His6-Op2-ratOp3-Op4
   61  LVDGQEAENLFPYTTRPKREGGQTFSLQSEVNITQGQWMSSNTYTCHVKH--NGSIFEDS  His6-Op2-Mouse3-Op4
   61  LVDGQEAENLFPYTTRPKREGGQTFSLQSEVNITQGQWMSSNTYTCHVKH--NGSIFEDS  His6-Op2-3-4
   60  LVDGQKAENLFPYTAPPKREGNRSFSSHSEVNITQDQWLSGKTFTCQVTHLADKKTYQDS  His6-Platypus C2-C3-C4

119  SRRCSDDEPRGVITYLIPPSPLDLYENGTPKLTCLVLDLESEENITVWRERKKSIGSA    His6-OpC2-RatC3-OpC4
  119  SRRCSDDEPRGVITYLIPPSPLDLYENGTPKLTCLVLDLESEENITVWRERKKSIGSA    His6-Op2-ratOp3-Op4
  119  SRRCPDHEPRGVITYLIPPSPLDLYQNGAPKLTCLVVDLESEKNVNVTWNQEKTSV-SA   His6-Op2-Mouse3-Op4
  119  AQKCSDTDPRGISAYILPPTPQDLFVKKVPTIGCLIVDLASAENVKVTWSRESGGPV-NP  His6-Op2-3-4
  120  APKCADSDPRGITVFLTPPSPTDLYISKTPKLTCLIIDLVSTEGMEVTWSRESGTPL-SA  His6-Platypus C2-C3-C4
```

```
     190       200       210       220       230       240
179 SQRSTKHHN-ATTSITSILPVDAKDWIEGEGYQCRVDHPHFPKPIVRSITKLPGKRLAPE  His6-OpC2-RatC3-OpC4
179 RSLVVKEQYNGTFTVTSHLPVNTDDWIEGDTYTCPLESPDMPVPLIRTISKAPGKRLAPE  His6-Op2-ratOp3-Op4
178 SQWYTKHHNNATTSITSILPVVAKDWIEGYGYQCIVDHPDFPKPIVRSITKLPGKRLAPE  His6-Op2-Mouse3-Op4
178 SSLVVKEQYNGTFTVTSHLPVNTDDWIEGDTYTCRLESPDMPVPLIRTISKAPGKRLAPE  His6-Op2-3-4
179 ESFEEQKQFNGTMSFISTVPVNIQDWNEGESYTCRVAHPDLPSPIIKTVTKLPGKRLAPE  His6-Platypus C2-C3-C4

250       260       270       280       290       300
238 VYMLPPSPEET--GTTRTVTCLIRGFYPSEISVQWLFNNEEDHTGHHTTRPQKDHGTDP   His6-OpC2-RatC3-OpC4
239 VYMLPPSPEET--GTTRTVTCLIRGFYPSEISVQWLFNNEEDHTGHHTTRPQKDHGTDP   His6-Op2-ratOp3-Op4
238 VYMLPPSPEET--GTTRTVTCLIRGFYPSEISVQWLFNNEEDHTGHHTTRPQKDHGTDP   His6-Op2-Mouse3-Op4
238 VYMLPPSPEET--GTTRTVTCLIRGFYPSEISVQWLFNNEEDHTGHHTTRPQKDHGTDP   His6-Op2-3-4
239 VYAFPPHQAEVSHGASLSLTCLIRGFYPENISVRWLLDNKPLPTEHYRTTKPLKDQGPDP  His6-Platypus C2-C3-C4

310       320       330       340
296 SFFLYSRMLVNKSIWEKGNLVTCRVVHEALPGSRTLEKSLHYSAGN-   His6-OpC2-RatC3-OpC4
297 SFFLYSRMLVNKSIWEKGNLVTCRVVHEALPGSRTLEKSLHYSAGN-   His6-Op2-ratOp3-Op4
296 SFFLYSRMLVNKSIWEKGNLVTCRVVHEALPGSRTLEKSLHYSAGN-   His6-Op2-Mouse3-Op4
296 SFFLYSRMLVNKSIWEKGNLVTCRVVHEALPGSRTLEKSLHYSAGN-   His6-Op2-3-4
299 AYFLYSRLAVNKSTWEQGNVYTCQVVHEALP-SRNTERKFQHTSGN-   His6-Platypus C2-C3-C4
```

*Fig. 2a2*

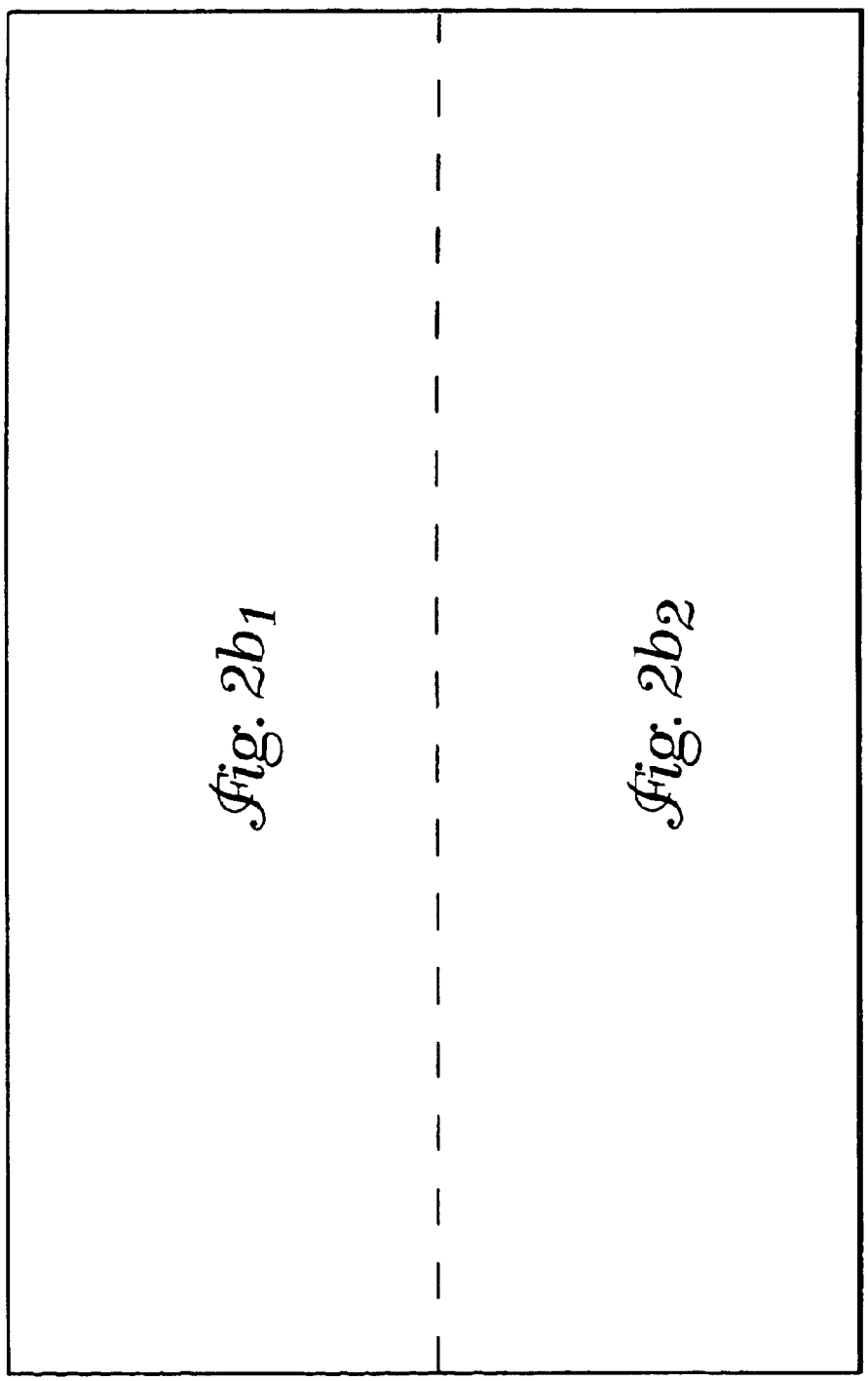

Fig. 2b₁

```
            10         20         30         40         50         60
     EFHHHHHHTLSLPESGPVTIIPPTVKLFHSSCDPRGDAHSTIQLLCLVSGFSPAKVHVTW  His6-OpC2-HumanC3-OpC4
  1  EFHHHHHHTLSLPESGPVTIIPPTVKLFHSSCDPRGDAHSTIQLLCLVSGFSPAKVHVTW  His6-OpC2-RatC3-OpC4
  1  EFHHHHHHTLSLPESGPVTIIPPTVKLFHSSCDPRGDAHSTIQLLCLVSGFSPAKVHVTW  His6-OpC2-PigC3-OpC4
  1  EFHHHHHHTLSLPESGPVTIIPPTVKLFHSSCDPRGDAHSTIQLLCLVSGFSPAKVHVTW  His6-OpC2-DogC3-OpC4
  1  EFHHHHHHTLSLPESGPVTIIPPTVKLFHSSCDPRGDAHSTIQLLCLVSGFSPAKVHVTW  His6-Op2-3-4
  1  EFHHHHHHTLSLPESGPVTIIPPTVKLFHSSCDPRGDAHSTIQLLCLVSGFSPAKVHVTW 70         80         90        100        110    ↓120
     LVDGQEAENLFPYTTRPKREGGQTFSLQSEVNITQGQWMSSNTYTCHVKHNGSIFEDSSR  His6-OpC2-HumanC3-OpC4
 61  LVDGQEAENLFPYTTRPKREGGQTFSLQSEVNITQGQWMSSNTYTCHVKHNGSIFEDSSR  His6-OpC2-RatC3-OpC4
 61  LVDGQEAENLFPYTTRPKREGGQTFSLQSEVNITQGQWMSSNTYTCHVKHNGSIFEDSSR  His6-OpC2-PigC3-OpC4
 61  LVDGQEAENLFPYTTRPKREGGQTFSLQSEVNITQGQWMSSNTYTCHVKHNGSIFEDSSR  His6-OpC2-DogC3-OpC4
 61  LVDGQEAENLFPYTTRPKREGGQTFSLQSEVNITQGQWMSSNTYTCHVKHNGSIFEDSAQ  His6-Op2-3-4
 61  LVDGQEAENLFPYTTRPKREGGQTFSLQSEVNITQGQWMSSNTYTCHVKHNGSIFEDSAQ 130        140        150        160        170        180
     KC-ADSNPRGVSAYLSRPSPFDLFIRKSPTITCLVVDLAPSKGTVNLTWSRASGKPV---  His6-OpC2-HumanC3-OpC4
121  RCS-DDEPRGVITYLIPPSPLDLYENGTPKLTCLVLDLES-EENITVTWVRERKKSI---  His6-OpC2-RatC3-OpC4
121  RCTAESEPRGVSAYLSPPTPLDLYVHKSPKLTCLVVDLASSEN-VNLLWSRENKGGVILP  His6-OpC2-PigC3-OpC4
121  KCS-ESDPRGVTSYLSPPSPLDLYVHKAPKITCLVVDLATMEG-MNLTWYRESKEPV---  His6-OpC2-DogC3-OpC4
121  KCS-DTDPRGISAYILPPTPQDLFVKKVPTIGCLIVDLASAEN-VKVTWSRESGGPV---  His6-Op2-3-4
```

```
177 NHSTRKEEKQRNGTLTVTSTLPVGTRDWIEGETYQCRVTHPHLPRALMRSTTKLPGKRLA  His6-OpC2-HumanC3-OpC4
176 GSASQRSTKHHNATTSITSILPVDAKDWIEGEGYQCRVDHPHFPKPIVRSITKLPGKRLA  His6-OpC2-RatC3-OpC4
180 PPGPPVIKPQFNGTFSATSTLPVNVSDWIEGETYYCNVTHPDLPKPILRSISKLPGKRLA  His6-OpC2-PigC3-OpC4
176 NPGPLNKKDHFNGTITVTSTLPVNTNDWIEGETYYCRVTHPHLPKDIVRSIAKLPGKRLA  His6-OpC2-DogC3-OpC4
176 NPSSLVVKEQYNGTFTVTSHLPVNTDDWIEGDTYTCRLESPDMPVPLIRTISKAPGKRLA  His6-Op2-3-4
                                            ↓
         190       200       210       220       230       240

237 PEVYMLPPSPEETGTTRTVTCLIRGFYPSEISVQWLFNNEEDHTGHHTTRPQKDHGTDP  His6-OpC2-HumanC3-OpC4
236 PEVYMLPPSPEETGTTRTVTCLIRGFYPSEISVQWLFNNEEDHTGHHTTRPQKDHGTDP  His6-OpC2-RatC3-OpC4
240 PEVYMLPPSPEETGTTRTVTCLIRGFYPSEISVQWLFNNEEDHTGHHTTRPQKDHGTDP  His6-OpC2-PigC3-OpC4
236 PEVYMLPPSPEETGTTRTVTCLIRGFYPSEISVQWLFNNEEDHTGHHTTRPQKDHGTDP  His6-OpC2-DogC3-OpC4
236 PEVYMLPPSPEETGTTRTVTCLIRGFYPSEISVQWLFNNEEDHTGHHTTRPQKDHGTDP  His6-Op2-3-4

250       260       270       280       290       300

297 SFFLYSRMLVNKSIWEKGNLVTCRVVHEALPGSRTLEKSLHYSAGN  His6-OpC2-HumanC3-OpC4
296 SFFLYSRMLVNKSIWEKGNLVTCRVVHEALPGSRTLEKSLHYSAGN  His6-OpC2-RatC3-OpC4
300 SFFLYSRMLVNKSIWEKGNLVTCRVVHEALPGSRTLEKSLHYSAGN  His6-OpC2-PigC3-OpC4
296 SFFLYSRMLVNKSIWEKGNLVTCRVVHEALPGSRTLEKSLHYSAGN  His6-OpC2-DogC3-OpC4
296 SFFLYSRMLVNKSIWEKGNLVTCRVVHEALPGSRTLEKSLHYSAGN  His6-Op2-3-4

310       320       330       340
```

*Fig. 2b₂*

SEQUENCE LISTING

```
<160> NUMBER OF SEQ ID NOS:  11

<210> SEQ ID NO 1
<211> LENGTH: 331
<212> TYPE: PRT
<213> ORGANISM: Artificial Sequence
<220> FEATURE:
<223> OTHER INFORMATION: Synthetically generated proteins

<400> SEQUENCE: 1

Asp Asn Lys Thr Phe Ser Val Cys Ser Arg Asp Phe Thr Pro Pro Thr
 1               5                  10                  15

Val Lys Ile Leu Gln Ser Ser Cys Asp Gly Gly Gly His Phe Pro Pro
```

-continued

```
                   20                  25                  30
    Thr Ile Gln Leu Leu Cys Leu Val Ser Gly Tyr Thr Pro Gly Thr Ile
                35                  40                  45
    Asn Ile Thr Trp Leu Glu Asp Gly Gln Val Met Asp Val Asp Leu Ser
             50                  55                  60
    Thr Ala Ser Thr Thr Gln Glu Gly Glu Leu Ala Ser Thr Gln Ser Glu
     65                  70                  75                  80
    Leu Thr Leu Ser Gln Lys His Trp Leu Ser Asp Arg Thr Tyr Thr Cys
                     85                  90                  95
    Gln Val Thr Tyr Gln Gly His Thr Phe Glu Asp Ser Thr Lys Lys Cys
                    100                 105                 110
    Ala Asp Ser Asn Pro Arg Gly Val Ser Ala Tyr Leu Ser Arg Pro Ser
                    115                 120                 125
    Pro Phe Asp Leu Phe Ile Arg Lys Ser Pro Thr Ile Thr Cys Leu Val
                    130                 135                 140
    Val Asp Leu Ala Pro Ser Lys Gly Thr Val Asn Leu Thr Trp Ser Arg
    145                 150                 155                 160
    Ala Ser Gly Lys Pro Val Asn His Ser Thr Arg Lys Glu Glu Lys Gln
                    165                 170                 175
    Arg Asn Gly Thr Leu Thr Val Thr Ser Thr Leu Pro Val Gly Thr Arg
                    180                 185                 190
    Asp Trp Ile Glu Gly Glu Thr Tyr Gln Cys Arg Val Thr His Pro His
                    195                 200                 205
    Leu Pro Arg Ala Leu Met Arg Ser Thr Thr Lys Thr Ser Gly Pro Arg
                    210                 215                 220
    Ala Ala Pro Glu Val Tyr Ala Phe Ala Thr Pro Glu Trp Pro Gly Ser
    225                 230                 235                 240
    Arg Asp Lys Arg Thr Leu Ala Cys Leu Ile Gln Asn Phe Met Pro Glu
                    245                 250                 255
    Asp Ile Ser Val Gln Trp Leu His Asn Glu Val Gln Leu Pro Asp Ala
                    260                 265                 270
    Arg His Ser Thr Thr Gln Pro Arg Lys Thr Lys Gly Ser Gly Phe Phe
                    275                 280                 285
    Val Phe Ser Arg Leu Glu Val Thr Arg Ala Glu Trp Glu Gln Lys Asp
                    290                 295                 300
    Glu Phe Ile Cys Arg Ala Val His Glu Ala Ala Ser Pro Ser Gln Thr
    305                 310                 315                 320
    Val Gln Arg Ala Val Ser Val Asn Pro Gly Lys
                    325                 330

<210> SEQ ID NO 2
<211> LENGTH: 340
<212> TYPE: PRT
<213> ORGANISM: Artificial Sequence
<220> FEATURE:
<223> OTHER INFORMATION: Synthetically generated proteins

<400> SEQUENCE: 2

Asp Leu Thr Ile Arg Ala Arg Pro Val Asn Ile Thr Lys Pro Thr Val
  1               5                  10                  15
Asp Leu Leu His Ser Ser Cys Asp Pro Asn Ala Phe His Ser Thr Ile
                 20                  25                  30
Gln Leu Tyr Cys Phe Val Tyr Gly His Ile Gln Asn Asp Val Ser Ile
             35                  40                  45
His Trp Leu Met Asp Asp Arg Lys Ile Tyr Glu Thr His Ala Gln Asn
```

-continued

```
            50                  55                  60
Val Leu Ile Lys Glu Gly Lys Leu Ala Ser Thr Tyr Ser Arg Leu
 65                  70                  75                  80

Asn Ile Thr Gln Gln Gln Trp Met Ser Glu Ser Thr Phe Thr Cys Lys
                 85                  90                  95

Val Thr Ser Gln Gly Glu Asn Tyr Trp Ala His Thr Arg Arg Cys Ser
                100                 105                 110

Asp Asp Glu Pro Arg Gly Val Ile Thr Tyr Leu Ile Pro Pro Ser Pro
                115                 120                 125

Leu Asp Leu Tyr Glu Asn Gly Thr Pro Lys Leu Thr Cys Leu Val Leu
130                 135                 140

Asp Leu Glu Ser Glu Glu Asn Ile Thr Val Thr Trp Val Arg Glu Arg
145                 150                 155                 160

Lys Lys Ser Ile Gly Ser Ala Ser Gln Arg Ser Thr Lys His His Asn
                165                 170                 175

Ala Thr Thr Ser Ile Thr Ser Ile Leu Pro Val Asp Ala Lys Asp Trp
                180                 185                 190

Ile Glu Gly Glu Gly Tyr Gln Cys Arg Val Asp His Pro His Phe Pro
                195                 200                 205

Lys Pro Ile Val Arg Ser Ile Thr Lys Ala Pro Gly Lys Arg Ser Ala
210                 215                 220

Pro Glu Val Tyr Val Phe Leu Pro Pro Glu Glu Glu Lys Asp Lys
225                 230                 235                 240

Arg Thr Leu Thr Cys Leu Ile Gln Asn Phe Phe Pro Glu Asp Ile Ser
                245                 250                 255

Val Gln Trp Leu Gln Asp Ser Lys Leu Ile Pro Lys Ser Gln His Ser
                260                 265                 270

Thr Thr Thr Pro Leu Lys Tyr Asn Gly Ser Asn Gln Arg Phe Phe Ile
                275                 280                 285

Phe Ser Arg Leu Glu Val Thr Lys Ala Leu Trp Thr Gln Thr Lys Gln
                290                 295                 300

Phe Thr Cys Arg Val Ile His Glu Ala Leu Arg Glu Pro Arg Lys Leu
305                 310                 315                 320

Glu Arg Thr Ile Ser Lys Ser Leu Gly Asn Thr Ser Leu Arg Pro Ser
                325                 330                 335

Gln Ala Ser Met
                340

<210> SEQ ID NO 3
<211> LENGTH: 341
<212> TYPE: PRT
<213> ORGANISM: Artificial Sequence
<220> FEATURE:
<223> OTHER INFORMATION: Synthetically generated proteins

<400> SEQUENCE: 3

Glu Phe His His His His His Thr Leu Ser Leu Pro Glu Ser Gly
  1               5                  10                  15

Pro Val Thr Ile Ile Pro Pro Thr Val Lys Leu Phe His Ser Ser Cys
                 20                  25                  30

Asp Pro Arg Gly Asp Ala His Ser Thr Ile Gln Leu Leu Cys Leu Val
             35                  40                  45

Ser Gly Phe Ser Pro Ala Lys Val His Val Thr Trp Leu Val Asp Gly
         50                  55                  60

Gln Glu Ala Glu Asn Leu Phe Pro Tyr Thr Thr Arg Pro Lys Arg Glu
```

-continued

```
                65                  70                  75                  80
Gly Gly Gln Thr Phe Ser Leu Gln Ser Glu Val Asn Ile Thr Gln Gly
                85                  90                  95
Gln Trp Met Ser Ser Asn Thr Tyr Thr Cys His Val Lys His Asn Gly
           100                 105                 110
Ser Ile Phe Glu Asp Ser Ala Gln Lys Cys Ser Asp Thr Asp Pro Arg
           115                 120                 125
Gly Ile Ser Ala Tyr Ile Leu Pro Pro Thr Pro Gln Asp Leu Phe Val
           130                 135                 140
Lys Lys Val Pro Thr Ile Gly Cys Leu Ile Val Asp Leu Ala Ser Ala
145                 150                 155                 160
Glu Asn Val Lys Val Thr Trp Ser Arg Glu Ser Gly Gly Pro Val Asn
                165                 170                 175
Pro Ser Ser Leu Val Val Lys Glu Gln Tyr Asn Gly Thr Phe Thr Val
                180                 185                 190
Thr Ser His Leu Pro Val Asn Thr Asp Asp Trp Ile Glu Gly Asp Thr
                195                 200                 205
Tyr Thr Cys Arg Leu Glu Ser Pro Asp Met Pro Val Pro Leu Ile Arg
           210                 215                 220
Thr Ile Ser Lys Ala Pro Gly Lys Arg Leu Ala Pro Glu Val Tyr Met
225                 230                 235                 240
Leu Pro Pro Ser Pro Glu Thr Gly Thr Thr Arg Thr Val Thr Cys
                245                 250                 255
Leu Ile Arg Gly Phe Tyr Pro Ser Glu Ile Ser Val Gln Trp Leu Phe
           260                 265                 270
Asn Asn Glu Glu Asp His Thr Gly His His Thr Thr Arg Pro Gln
           275                 280                 285
Lys Asp His Gly Thr Asp Pro Ser Phe Phe Leu Tyr Ser Arg Met Leu
           290                 295                 300
Val Asn Lys Ser Ile Trp Glu Lys Gly Asn Leu Val Thr Cys Arg Val
305                 310                 315                 320
Val His Glu Ala Leu Pro Gly Ser Arg Thr Leu Glu Lys Ser Leu His
                325                 330                 335
Tyr Ser Ala Gly Asn
           340

<210> SEQ ID NO 4
<211> LENGTH: 341
<212> TYPE: PRT
<213> ORGANISM: Artificial Sequence
<220> FEATURE:
<223> OTHER INFORMATION: Synthetically generated proteins

<400> SEQUENCE: 4

Glu Phe His His His His His His Thr Leu Ser Leu Pro Glu Ser Gly
1               5                   10                  15
Pro Val Thr Ile Ile Pro Pro Thr Val Lys Leu Phe His Ser Ser Cys
                20                  25                  30
Asp Pro Arg Gly Asp Ala His Ser Thr Ile Gln Leu Leu Cys Leu Val
           35                  40                  45
Ser Gly Phe Ser Pro Ala Lys Val His Val Thr Trp Leu Val Asp Gly
      50                  55                  60
Gln Glu Ala Glu Asn Leu Phe Pro Tyr Thr Thr Arg Pro Lys Arg Glu
65                  70                  75                  80
Gly Gly Gln Thr Phe Ser Leu Gln Ser Glu Val Asn Ile Thr Gln Gly
```

-continued

```
                    85                  90                  95
Gln Trp Met Ser Ser Asn Thr Tyr Thr Cys His Val Lys His Asn Gly
                100                 105                 110
Ser Ile Phe Glu Asp Ser Ser Arg Arg Cys Ser Asp Asp Glu Pro Arg
            115                 120                 125
Gly Val Ile Thr Tyr Leu Ile Pro Ser Pro Leu Asp Leu Tyr Glu
        130                 135                 140
Asn Gly Thr Pro Lys Leu Thr Cys Leu Val Leu Asp Leu Glu Ser Glu
145                 150                 155                 160
Glu Asn Ile Thr Val Thr Trp Val Arg Glu Arg Lys Lys Ser Ile Gly
                165                 170                 175
Ser Ala Ser Gln Arg Ser Thr Lys His His Ala Thr Thr Ser Ile
            180                 185                 190
Thr Ser Ile Leu Pro Val Asp Ala Lys Asp Trp Ile Glu Gly Glu Gly
        195                 200                 205
Tyr Gln Cys Arg Val Asp His Pro His Phe Pro Lys Pro Ile Val Arg
    210                 215                 220
Ser Ile Thr Lys Leu Pro Gly Lys Arg Leu Ala Pro Glu Val Tyr Met
225                 230                 235                 240
Leu Pro Pro Ser Pro Glu Glu Thr Gly Thr Thr Arg Thr Val Thr Cys
                245                 250                 255
Leu Ile Arg Gly Phe Tyr Pro Ser Glu Ile Ser Val Gln Trp Leu Pro
            260                 265                 270
Asn Asn Glu Glu Asp His Thr Gly His His Thr Thr Thr Arg Pro Gln
        275                 280                 285
Lys Asp His Gly Thr Asp Pro Ser Phe Phe Leu Tyr Ser Arg Met Leu
    290                 295                 300
Val Asn Lys Ser Ile Trp Glu Lys Gly Asn Leu Val Thr Cys Arg Val
305                 310                 315                 320
Val His Glu Ala Leu Pro Gly Ser Arg Thr Leu Glu Lys Ser Leu His
                325                 330                 335
Tyr Ser Ala Gly Asn
            340
```

<210> SEQ ID NO 5
<211> LENGTH: 342
<212> TYPE: PRT
<213> ORGANISM: Artificial Sequence
<220> FEATURE:
<223> OTHER INFORMATION: Synthetically generated proteins

<400> SEQUENCE: 5

```
Glu Phe His His His His His Thr Leu Ser Leu Pro Glu Ser Gly
1               5                   10                  15
Pro Val Thr Ile Ile Pro Pro Thr Val Lys Leu Phe His Ser Ser Cys
                20                  25                  30
Asp Pro Arg Gly Asp Ala His Ser Thr Ile Gln Leu Leu Cys Leu Val
            35                  40                  45
Ser Gly Phe Ser Pro Ala Lys Val His Val Thr Trp Leu Val Asp Gly
        50                  55                  60
Gln Glu Ala Glu Asn Leu Phe Pro Tyr Thr Thr Arg Pro Lys Arg Glu
65                  70                  75                  80
Gly Gly Gln Thr Phe Ser Leu Gln Ser Glu Val Asn Ile Thr Gln Gly
                85                  90                  95
Gln Trp Met Ser Ser Asn Thr Tyr Thr Cys His Val Lys His Asn Gly
```

```
                100             105             110
Ser Ile Phe Glu Asp Ser Ser Arg Arg Cys Ser Asp Asp Glu Pro Arg
        115                 120                 125
Gly Val Ile Thr Tyr Leu Ile Pro Pro Ser Pro Leu Asp Leu Tyr Glu
    130                 135                 140
Asn Gly Thr Pro Lys Leu Thr Cys Leu Val Leu Asp Leu Glu Ser Glu
145                 150                 155                 160
Glu Asn Ile Thr Val Thr Trp Val Arg Glu Arg Lys Lys Ser Ile Gly
                165                 170                 175
Ser Ala Arg Ser Leu Val Val Lys Glu Gln Tyr Asn Gly Thr Phe Thr
            180                 185                 190
Val Thr Ser His Leu Pro Val Asn Thr Asp Asp Trp Ile Glu Gly Asp
                195                 200                 205
Thr Tyr Thr Cys Arg Leu Glu Ser Pro Asp Met Pro Tyr Pro Leu Ile
    210                 215                 220
Arg Thr Ile Ser Lys Ala Pro Gly Lys Arg Leu Ala Pro Glu Val Tyr
225                 230                 235                 240
Met Leu Pro Pro Ser Pro Glu Glu Thr Gly Thr Thr Arg Thr Val Thr
                245                 250                 255
Cys Leu Ile Arg Gly Phe Tyr Pro Ser Glu Ile Ser Val Gln Trp Leu
            260                 265                 270
Pro Asn Asn Glu Glu Asp His Thr Gly His His Thr Thr Thr Arg Pro
                275                 280                 285
Gln Lys Asp His Gly Thr Asp Pro Ser Phe Phe Leu Tyr Ser Arg Met
    290                 295                 300
Leu Val Asn Lys Ser Ile Trp Glu Lys Gly Asn Leu Val Thr Cys Arg
305                 310                 315                 320
Val Val His Glu Ala Leu Pro Gly Ser Arg Thr Leu Glu Lys Ser Leu
                325                 330                 335
His Tyr Ser Ala Gly Asn
            340

<210> SEQ ID NO 6
<211> LENGTH: 341
<212> TYPE: PRT
<213> ORGANISM: Artificial Sequence
<220> FEATURE:
<223> OTHER INFORMATION: Synthetically generated proteins

<400> SEQUENCE: 6

Glu Phe His His His His His His Thr Leu Ser Leu Pro Glu Ser Gly
  1               5                  10                  15
Pro Val Thr Ile Ile Pro Pro Thr Val Lys Leu Phe His Ser Ser Cys
            20                  25                  30
Asp Pro Arg Gly Asp Ala His Ser Thr Ile Gln Leu Leu Cys Leu Val
        35                  40                  45
Ser Gly Phe Ser Pro Ala Lys Val His Val Thr Trp Leu Val Asp Gly
    50                  55                  60
Gln Glu Ala Glu Asn Leu Phe Pro Tyr Thr Thr Arg Pro Lys Arg Glu
65                  70                  75                  80
Gly Gly Gln Thr Phe Ser Leu Gln Ser Glu Val Asn Ile Thr Gln Gly
                85                  90                  95
Gln Trp Met Ser Ser Asn Thr Tyr Thr Cys His Val Lys His Asn Gly
            100                 105                 110
Ser Ile Phe Glu Asp Ser Ser Arg Arg Cys Pro Asp His Glu Pro Arg
```

```
            115                 120                     125
Gly Val Ile Thr Tyr Leu Ile Pro Pro Ser Pro Leu Asp Leu Tyr Gln
        130                 135                 140

Asn Gly Ala Pro Lys Leu Thr Cys Leu Val Asp Leu Glu Ser Glu
145                 150                 155                 160

Lys Asn Val Asn Val Thr Trp Asn Gln Glu Lys Lys Thr Ser Val Asn
                165                 170                 175

Ala Ser Gln Trp Tyr Thr Lys His His Asn Asn Ala Thr Thr Ser Ile
            180                 185                 190

Thr Ser Ile Leu Pro Val Val Ala Lys Asp Trp Ile Glu Gly Tyr Gly
            195                 200                 205

Tyr Gln Cys Ile Val Asp His Pro Asp Phe Pro Lys Pro Ile Val Arg
        210                 215                 220

Ser Ile Thr Lys Leu Pro Gly Lys Arg Leu Ala Pro Glu Val Tyr Met
225                 230                 235                 240

Leu Pro Pro Ser Pro Glu Glu Thr Gly Thr Thr Arg Thr Val Thr Cys
                245                 250                 255

Leu Ile Arg Gly Phe Tyr Pro Ser Glu Ile Ser Val Gln Trp Leu Pro
            260                 265                 270

Asn Asn Glu Glu Asp His Thr Gly His His Thr Thr Arg Pro Gln
            275                 280                 285

Lys Asp His Gly Thr Asp Pro Ser Phe Phe Leu Tyr Ser Arg Met Leu
        290                 295                 300

Val Asn Lys Ser Ile Trp Glu Lys Gly Asn Leu Val Thr Cys Arg Val
305                 310                 315                 320

Val His Glu Ala Leu Pro Gly Ser Arg Thr Leu Glu Lys Ser Leu His
                325                 330                 335

Tyr Ser Ala Gly Asn
            340

<210> SEQ ID NO 7
<211> LENGTH: 343
<212> TYPE: PRT
<213> ORGANISM: Artificial Sequence
<220> FEATURE:
<223> OTHER INFORMATION: Synthetically generated proteins

<400> SEQUENCE: 7

Glu Phe His His His His His Thr Glu Val Tyr Ser Asp Ser Ser
1               5                   10                  15

Lys Asp Pro Ile Pro Pro Thr Val Lys Leu Leu His Ser Ser Cys Asp
                20                  25                  30

Pro Arg Gly Asp Ser Gln Ala Ser Ile Glu Leu Leu Cys Leu Ile Thr
            35                  40                  45

Gly Tyr Ser Pro Ala Gly Ile Gln Val Asp Trp Leu Val Asp Gly Gln
        50                  55                  60

Lys Ala Glu Asn Leu Phe Pro Tyr Thr Ala Pro Lys Arg Glu Gly
65                  70                  75                  80

Asn Arg Ser Phe Ser Ser His Ser Glu Val Asn Ile Thr Gln Asp Gln
                85                  90                  95

Trp Leu Ser Gly Lys Thr Phe Thr Cys Gln Val Thr His Leu Ala Asp
            100                 105                 110

Lys Lys Thr Tyr Gln Asp Ser Ala Pro Lys Cys Ala Asp Ser Asp Pro
        115                 120                 125

Arg Gly Ile Thr Val Phe Ile Thr Pro Pro Ser Pro Thr Asp Leu Tyr
```

```
                130                 135                 140
Ile Ser Lys Thr Pro Lys Leu Thr Cys Leu Ile Ile Asp Leu Val Ser
145                 150                 155                 160

Thr Glu Gly Met Glu Val Thr Trp Ser Arg Glu Ser Gly Thr Pro Leu
                165                 170                 175

Ser Ala Glu Ser Phe Glu Glu Gln Lys Gln Phe Asn Gly Thr Met Ser
                180                 185                 190

Phe Ile Ser Thr Val Pro Val Asn Ile Gln Asp Trp Asn Arg Gly Glu
            195                 200                 205

Ser Tyr Thr Cys Pro Val Ala His Pro Asp Leu Pro Ser Pro Ile Ile
        210                 215                 220

Lys Thr Val Thr Lys Leu Pro Gly Lys Pro Leu Ala Pro Glu Val Tyr
225                 230                 235                 240

Ala Phe Pro Pro His Gln Ala Glu Val Ser His Gly Ala Ser Leu Ser
                245                 250                 255

Leu Thr Cys Leu Ile Pro Gly Phe Tyr Pro Glu Asn Ile Ser Val Arg
                260                 265                 270

Trp Leu Leu Asp Asn Lys Pro Leu Pro Thr Glu His Tyr Arg Thr Thr
            275                 280                 285

Lys Pro Leu Lys Asp Gln Gly Pro Asp Pro Ala Tyr Phe Leu Tyr Ser
        290                 295                 300

Pro Leu Ala Val Asn Lys Ser Thr Trp Glu Gln Gly Asn Val Tyr Thr
305                 310                 315                 320

Cys Gln Val Val His Glu Ala Leu Pro Ser Arg Asn Thr Glu Arg Lys
                325                 330                 335

Phe Gln His Thr Ser Gly Asn
            340

<210> SEQ ID NO 8
<211> LENGTH: 342
<212> TYPE: PRT
<213> ORGANISM: Artificial Sequence
<220> FEATURE:
<223> OTHER INFORMATION: Synthetically generated proteins

<400> SEQUENCE: 8

Glu Phe His His His His His Thr Leu Ser Leu Pro Glu Ser Gly
  1               5                  10                  15

Pro Val Thr Ile Ile Pro Pro Thr Val Lys Leu Phe His Ser Ser Cys
                20                  25                  30

Asp Pro Arg Gly Asp Ala His Ser Thr Ile Gln Leu Leu Cys Leu Val
            35                  40                  45

Ser Gly Phe Ser Pro Ala Lys Val His Val Thr Trp Leu Val Asp Gly
        50                  55                  60

Gln Glu Ala Glu Asn Leu Phe Pro Tyr Thr Thr Arg Pro Lys Arg Glu
65                  70                  75                  80

Gly Gly Gln Thr Phe Ser Leu Gln Ser Glu Val Asn Ile Thr Gln Gly
                85                  90                  95

Gln Trp Met Ser Ser Asn Thr Tyr Thr Cys His Val Lys His Asn Gly
                100                 105                 110

Ser Ile Phe Glu Asp Ser Ser Arg Lys Cys Ala Asp Ser Asn Pro Arg
            115                 120                 125

Gly Val Ser Ala Tyr Leu Ser Arg Pro Ser Pro Phe Asp Leu Phe Ile
        130                 135                 140

Arg Lys Ser Pro Thr Ile Thr Cys Leu Val Val Asp Leu Ala Pro Ser
```

-continued

```
            145                 150                 155                 160
Lys Gly Thr Val Asn Leu Thr Trp Ser Arg Ala Ser Gly Lys Pro Val
                165                 170                 175

Asn His Ser Thr Arg Lys Glu Lys Gln Arg Asn Gly Thr Leu Thr
                180                 185                 190

Val Thr Ser Thr Leu Pro Val Gly Thr Arg Asp Trp Ile Glu Gly Glu
                195                 200                 205

Thr Tyr Gln Cys Arg Val Thr His Pro His Leu Pro Arg Ala Leu Met
            210                 215                 220

Arg Ser Thr Thr Lys Leu Pro Gly Lys Arg Leu Ala Pro Glu Val Tyr
225                 230                 235                 240

Met Leu Pro Pro Ser Pro Glu Glu Thr Gly Thr Thr Arg Thr Val Thr
                245                 250                 255

Cys Leu Ile Arg Gly Phe Tyr Pro Ser Glu Ile Ser Val Gln Trp Leu
                260                 265                 270

Phe Asn Asn Glu Glu Asp His Thr Gly His His Thr Thr Thr Arg Pro
                275                 280                 285

Gln Lys Asp His Gly Thr Asp Pro Ser Phe Phe Leu Tyr Ser Arg Met
            290                 295                 300

Leu Val Asn Lys Ser Ile Trp Glu Lys Gly Asn Leu Val Thr Cys Arg
305                 310                 315                 320

Val Val His Glu Ala Leu Pro Gly Ser Arg Thr Leu Glu Lys Ser Leu
                325                 330                 335

His Tyr Ser Ala Gly Asn
            340

<210> SEQ ID NO 9
<211> LENGTH: 341
<212> TYPE: PRT
<213> ORGANISM: Artificial Sequence
<220> FEATURE:
<223> OTHER INFORMATION: Synthetically generated proteins

<400> SEQUENCE: 9

Glu Phe His His His His His Thr Leu Ser Leu Pro Glu Ser Gly
1               5                   10                  15

Pro Val Thr Ile Ile Pro Pro Thr Val Lys Leu Phe His Ser Ser Cys
                20                  25                  30

Asp Pro Arg Gly Asp Ala His Ser Thr Ile Gln Leu Leu Cys Leu Val
            35                  40                  45

Ser Gly Phe Ser Pro Ala Lys Val His Val Thr Trp Leu Val Asp Gly
        50                  55                  60

Gln Glu Ala Glu Asn Leu Phe Pro Tyr Thr Thr Arg Pro Lys Arg Glu
65                  70                  75                  80

Gly Gly Gln Thr Phe Ser Leu Gln Ser Glu Val Asn Ile Thr Gln Gly
                85                  90                  95

Gln Trp Met Ser Ser Asn Thr Tyr Thr Cys His Val Lys His Asn Gly
                100                 105                 110

Ser Ile Phe Glu Asp Ser Ser Arg Arg Cys Ser Asp Asp Glu Pro Arg
            115                 120                 125

Gly Val Ile Thr Tyr Leu Ile Pro Pro Ser Pro Leu Asp Leu Tyr Glu
        130                 135                 140

Asn Gly Thr Pro Lys Leu Thr Cys Leu Val Leu Asp Leu Glu Ser Glu
145                 150                 155                 160
```

```
Glu Asn Ile Thr Val Thr Trp Val Arg Glu Arg Lys Lys Ser Ile Gly
                165                 170                 175

Ser Ala Ser Gln Arg Ser Thr Lys His His Asn Ala Thr Thr Ser Ile
            180                 185                 190

Thr Ser Ile Leu Pro Val Asp Ala Lys Asp Trp Ile Glu Gly Glu Gly
        195                 200                 205

Tyr Gln Cys Arg Val Asp His Pro His Phe Pro Lys Pro Ile Val Arg
    210                 215                 220

Ser Ile Thr Lys Leu Pro Gly Lys Arg Leu Ala Pro Glu Val Tyr Met
225                 230                 235                 240

Leu Pro Pro Ser Pro Glu Glu Thr Gly Thr Thr Arg Thr Val Thr Cys
                245                 250                 255

Leu Ile Arg Gly Phe Tyr Pro Ser Glu Ile Ser Val Gln Trp Leu Phe
            260                 265                 270

Asn Asn Glu Glu Asp His Thr Gly His His Thr Thr Thr Arg Pro Gln
        275                 280                 285

Lys Asp His Gly Thr Asp Pro Ser Phe Phe Leu Tyr Ser Arg Met Leu
    290                 295                 300

Val Asn Lys Ser Ile Trp Glu Lys Gly Asn Leu Val Thr Cys Arg Val
305                 310                 315                 320

Val His Glu Ala Leu Pro Gly Ser Arg Thr Leu Glu Lys Ser Leu His
                325                 330                 335

Tyr Ser Ala Gly Asn
            340

<210> SEQ ID NO 10
<211> LENGTH: 345
<212> TYPE: PRT
<213> ORGANISM: Artificial Sequence
<220> FEATURE:
<223> OTHER INFORMATION: Synthetically generated proteins

<400> SEQUENCE: 10

Glu Phe His His His His His Thr Leu Ser Leu Pro Glu Ser Gly
 1               5                   10                  15

Pro Val Thr Ile Ile Pro Pro Thr Val Lys Leu Phe His Ser Ser Cys
            20                  25                  30

Asp Pro Arg Gly Asp Ala His Ser Thr Ile Gln Leu Leu Cys Leu Val
        35                  40                  45

Ser Gly Phe Ser Pro Ala Lys Val His Val Thr Trp Leu Val Asp Gly
    50                  55                  60

Gln Glu Ala Glu Asn Leu Phe Pro Tyr Thr Thr Arg Pro Lys Arg Glu
65                  70                  75                  80

Gly Gly Gln Thr Phe Ser Leu Gln Ser Glu Val Asn Ile Thr Gln Gly
                85                  90                  95

Gln Trp Met Ser Ser Asn Thr Tyr Thr Cys His Val Lys His Asn Gly
            100                 105                 110

Ser Ile Phe Glu Asp Ser Ser Arg Arg Cys Thr Ala Glu Ser Glu Pro
        115                 120                 125

Arg Gly Val Ser Ala Tyr Leu Ser Pro Pro Thr Pro Leu Asp Leu Tyr
    130                 135                 140

Val His Lys Ser Pro Lys Leu Thr Cys Leu Val Val Asp Leu Ala Ser
145                 150                 155                 160

Ser Glu Asn Val Asn Leu Leu Trp Ser Arg Glu Asn Lys Gly Gly Val
                165                 170                 175
```

-continued

```
Ile Leu Pro Pro Gly Pro Pro Val Ile Lys Pro Gln Phe Asn Gly
            180                 185                 190

Thr Phe Ser Ala Thr Ser Thr Leu Pro Val Asn Val Ser Asp Trp Ile
        195                 200                 205

Glu Gly Glu Thr Tyr Tyr Cys Asn Val Thr His Pro Asp Leu Pro Lys
    210                 215                 220

Pro Ile Leu Arg Ser Ile Ser Lys Leu Pro Gly Lys Arg Leu Ala Pro
225                 230                 235                 240

Glu Val Tyr Met Leu Pro Pro Ser Pro Glu Glu Thr Gly Thr Thr Arg
                245                 250                 255

Thr Val Thr Cys Leu Ile Arg Gly Phe Tyr Pro Ser Glu Ile Ser Val
            260                 265                 270

Gln Trp Leu Phe Asn Asn Glu Glu Asp His Thr Gly His His Thr Thr
        275                 280                 285

Thr Arg Pro Gln Lys Asp His Gly Thr Asp Pro Ser Phe Phe Leu Tyr
    290                 295                 300

Ser Arg Met Leu Val Asn Lys Ser Ile Trp Glu Lys Gly Asn Leu Val
305                 310                 315                 320

Thr Cys Arg Val Val His Glu Ala Leu Pro Gly Ser Arg Thr Leu Glu
                325                 330                 335

Lys Ser Leu His Tyr Ser Ala Gly Asn
            340                 345

<210> SEQ ID NO 11
<211> LENGTH: 341
<212> TYPE: PRT
<213> ORGANISM: Artificial Sequence
<220> FEATURE:
<223> OTHER INFORMATION: Synthetically generated proteins

<400> SEQUENCE: 11

Glu Phe His His His His His Thr Leu Ser Leu Pro Glu Ser Gly
  1               5                  10                  15

Pro Val Thr Ile Ile Pro Pro Thr Val Lys Leu Phe His Ser Ser Cys
                20                  25                  30

Asp Pro Arg Gly Asp Ala His Ser Thr Ile Gln Leu Leu Cys Leu Val
            35                  40                  45

Ser Gly Phe Ser Pro Ala Lys Val His Val Thr Trp Leu Val Asp Gly
        50                  55                  60

Gln Glu Ala Glu Asn Leu Phe Pro Tyr Thr Thr Arg Pro Lys Arg Glu
 65                 70                  75                  80

Gly Gly Gln Thr Phe Ser Leu Gln Ser Glu Val Asn Ile Thr Gln Gly
                85                  90                  95

Gln Trp Met Ser Ser Asn Thr Tyr Thr Cys His Val Lys His Asn Gly
            100                 105                 110

Ser Ile Phe Glu Asp Ser Ser Arg Lys Cys Ser Glu Ser Asp Pro Arg
        115                 120                 125

Gly Val Thr Ser Tyr Leu Ser Pro Ser Pro Leu Asp Leu Tyr Val
        130                 135                 140

His Lys Ala Pro Lys Ile Thr Cys Leu Val Val Asp Leu Ala Thr Met
145                 150                 155                 160

Glu Gly Met Asn Leu Thr Trp Tyr Arg Glu Ser Lys Glu Pro Val Asn
                165                 170                 175

Pro Gly Pro Leu Asn Lys Lys Asp His Phe Asn Gly Thr Ile Thr Val
            180                 185                 190
```

```
Thr Ser Thr Leu Pro Val Asn Thr Asn Asp Trp Ile Glu Gly Glu Thr
        195             200             205
Tyr Tyr Cys Arg Val Thr His Pro His Leu Pro Lys Asp Ile Val Arg
    210             215             220
Ser Ile Ala Lys Leu Pro Gly Lys Arg Leu Ala Pro Glu Val Tyr Met
225             230             235             240
Leu Pro Pro Ser Pro Glu Glu Thr Gly Thr Thr Arg Thr Val Thr Cys
            245             250             255
Leu Ile Arg Gly Phe Tyr Pro Ser Glu Ile Ser Val Gln Trp Leu Phe
            260             265             270
Asn Asn Glu Glu Asp His Thr Gly His His Thr Thr Thr Arg Pro Gln
        275             280             285
Lys Asp His Gly Thr Asp Pro Ser Phe Phe Leu Tyr Ser Arg Met Leu
    290             295             300
Val Asn Lys Ser Ile Trp Glu Lys Gly Asn Leu Val Thr Cys Arg Val
305             310             315             320
Val His Glu Ala Leu Pro Gly Ser Arg Thr Leu Glu Lys Ser Leu His
            325             330             335
Tyr Ser Ala Gly Asn
            340
```

IMMUNOGENIC POLYPEPTIDES FOR INDUCING ANTI-SELF IGE RESPONSES

RELATED APPLICATIONS

This application is a divisional application of U.S. patent application Ser. No. 09/401,636, filed Sep. 22, 1999, which claims priority from U.S. Provisional Application Ser. No. 60/106,652, filed Nov. 2, 1998.

BACKGROUND

1. Technical Field

The invention relates to methods and materials involved in the treatment of various diseases such as infections and IgE-related diseases. Specifically, the invention relates to methods and materials that can be used to vaccinate a mammal against specific self or non-self antigens. For example, the methods and materials described herein can be used to reduce the effects of IgE antibodies within a mammal.

2. Background Information

Mammals are susceptible to many diseases and illnesses including bacterial infections, viral infections, and IgE-related diseases such as allergies. In general, infections are characterized by the invasion and multiplication of microorganisms (e.g., bacteria, fungi, and viruses) within body tissues. Many types of infections can be treated or prevented by the use of vaccines. For example, the polio vaccine can prevent poliovirus infections. Typically, a vaccine is a suspension of attenuated or killed microorganisms.

IgE-related diseases are mediated by a class of immunoglobulin designated as immunoglobulin E (IgE). In fact, IgE antibodies are a major cause of hypersensitivity reactions found within the human population despite their normally very low concentration in human plasma (10–400 ng/mL). The effects are due to the interaction of IgE antibodies with the high-affinity receptor for IgE on mast cells and basophilic leukocytes. Cross-linking of two IgE receptors on the surface of these cell types, for example by allergen binding, initiates the release of a number of physiologically active substances such as histamine, PAF platelet activating factor), heparin, leukotrienes, prostaglandins, thromboxanes, and chemotactic factors for eosinophilic and neutrophilic granulocytes. Presumably, these mediators cause the direct symptoms of IgE-mediated allergic reactions (type I hypersensitivity). Disease conditions belonging to this group can include asthma, far allergies, pollen allergies, food allergies, and eczema.

The high-affinity receptor for IgE has been characterized. This receptor appears to be present on mast cells, basophilic leucocytes, eosinophils, monocytes, and Langerhan cells. In addition, the receptor is a complex of three different subunits (α, β, and γ chains). The α chain is localized mainly extra-cellularly and appears to interact with the IgE molecule. Previous studies of the epsilon chain of the IgE molecule have suggested that a region of 76 amino acids at the border between the CH2 and CH3 domains (CH refers to the constant domains in the heavy chain) is important for the interaction between the IgE molecule and its high-affinity receptor. In addition, a peptide corresponding to this region was shown to inhibit the interaction between native IgE and its high-affinity receptor in vitro at a molar ratio of nearly 1:1 compared to the whole CH2-CH3-CH4 region (Helm et al., *Nature* 331, 180–183 (1988)). This peptide was also shown to inhibit an IgE-mediated flare reaction in allergen stimulation. In this case, however, the concentration was about 10 times the concentration needed to exhibit the same inhibitory effect with native IgE (Helm et al., *Proc. Natl. Acad. Sci. USA* 86, 9465–9469 (1989)).

SUMMARY

The invention relates to methods and materials involved in the treatment and prevention of various diseases such as infections and IgE-related diseases. Specifically, the invention relates to methods and materials that can be used to vaccinate a mammal against specific self or non-self antigens. For example, the methods and materials described herein can be used to reduce the effects of IgE antibodies within a mammal by reducing the amount of total and receptor bound IgE antibodies in the mammal. Such methods and materials can be used to treat atopic allergies in mammals such as humans, dogs, and pigs.

The invention is based on the discovery that a vaccine conjugate can be designed to contain at least two polypeptides with each polypeptide having at least two similar amino acid segments such that the administration of the conjugate to a mammal can induce an immune response against at least a portion of one of the polypeptides. Such immune responses can be more potent than the responses induced by any of the polypeptides in an unconjugated form or any conjugate of polypeptides lacking at least two similar amino acid segments. Thus, the vaccine conjugates described herein can be used to provide mammals with substantial protection against a wide range of either self (e.g., IgE molecules) or non-self (e.g., viral polypeptides) antigens.

The invention also is based on the discovery that a vaccine conjugate can be designed to contain a polypeptide having a cytokine activity such that a potent immune response is induced against another polypeptide within the conjugate. Such immune responses can be more potent than the responses induced by a conjugate lacking a polypeptide having a cytokine activity. Although not limited to any particular mode of action, a conjugate containing a polypeptide having a cytokine activity as well as an immunogenic polypeptide presumably concentrates cytokine activity to the localized area containing the immunogenic polypeptide. Thus, the polypeptide having cytokine activity can stimulate cells that participate in generating a specific immune response against the immunogenic polypeptide.

In addition, the invention is based on the discovery that polypeptides containing a self IgE portion and a non-self IgE portion are immunogenic and induce an effective anti-self IgE response in mammals. Such immunogenic polypeptides can be used as a vaccine to induce an anti-self IgE response that counteracts the hypersensitivity induced by self IgE antibodies. Although not limited to any particular mode of action, the immunogenic polypeptides described herein induce the production of anti-self IgE antibodies that presumably have specificity for the portion of the IgE molecule that interacts with the high-affinity IgE receptor. After production, the anti-self IgE antibodies can interact with the self-IgE antibodies such that the self IgE antibodies are unable to bind to the high-affinity IgE receptor. This inhibition of receptor binding presumably reduces the hypersensitivity induced by self IgE antibodies. Thus, the degree of IgE-induced effects can be reduced as more anti-self IgE antibodies are produced.

In general, the invention features an immunogenic polypeptide having a self IgE portion and a non-self IgE portion. The immunogenic polypeptide is effective to induce an anti-self IgE response in a mammal (e.g., human). The self portion can contain at least a portion of a CH3 domain of IgE. The polypeptide can be capable of dimerizing to form a soluble immunogenic dimer effective to induce the anti-self IgE response in the mammal. The non-self IgE portion can contain a first region and a second region with the self IgE portion being located between the first and second regions of the non-self IgE portion. The first region can contain at least a portion of an IgE CH2 domain, and the second region can contain at least a portion of an IgE CH4 domain. The non-self IgE portion can contain an IgE sequence present in a non-placental mammal (e.g., opossum, platypus, koala, kangaroo, wallaby, and wombat). The self IgE portion can lack the CH2 domain of an IgE antibody. The immunogenic polypeptide can contain a eukaryotic post-translational modification. In addition, the immunogenic polypeptide can contain a polyhistidine sequence. The anti-self IgE response can be a polyclonal response.

In another embodiment, the invention features a nucleic acid molecule containing a nucleic acid sequence that encodes an immunogenic polypeptide. The immunogenic polypeptide contains a self IgE portion as well as a non-self IgE portion, and is effective to induce an anti-self IgE response in a mammal. The nucleic acid molecule can contain an additional nucleic acid sequence that encodes an amino acid sequence that promotes the secretion of the immunogenic polypeptide from a eukaryotic cell.

Another embodiment of the invention features a host cell (e.g., eukaryotic cell) containing a nucleic acid molecule that has a nucleic acid sequence that encodes an immunogenic polypeptide. The immunogenic polypeptide contains a self IgE portion as well as a non-self IgE portion, and is effective to induce an anti-self IgE response in a mammal.

Another embodiment of the invention features a soluble immunogenic dimer containing two immunogenic polypeptides that are capable of dimerizing to form the soluble immunogenic dimer. Each of the two immunogenic polypeptides contains a self IgE portion and a non-self IgE portion, and the soluble immunogenic dimer is effective to induce an anti-self IgE response in a mammal.

Another embodiment of the invention features a vaccine containing an immunogenic polypeptide having a self IgE portion and a non-self IgE portion. The immunogenic polypeptide is effective to induce an anti-self IgE response in a mammal. The vaccine can contain a pharmaceutically acceptable carrier.

Another embodiment of the invention features a method for making a nucleic acid molecule that encodes an immunogenic polypeptide effective to induce an anti-self IgE response in a mammal. The method includes combining first and second nucleic acid sequences to form the nucleic acid molecule, where the first nucleic acid sequence encodes at least a portion of an IgE molecule present within the mammal, and where the second nucleic acid sequence encodes at least a portion of an IgE molecule not present in the mammal.

Another embodiment of the invention features a method for making a nucleic acid molecule that encodes an immunogenic polypeptide effective to induce an anti-self IgE response in a mammal. The method includes (a) selecting a first nucleic acid sequence, where the first nucleic acid sequence encodes at least a portion of an IgE molecule present within the mammal, (b) selecting a second nucleic acid sequence, where the second nucleic acid sequence encodes at least a portion of an IgE molecule not present in the mammal, and (c) combining the first and second nucleic acid sequences to form the nucleic acid molecule.

In another aspect, the invention features a vaccine complex for vaccinating a mammal (e.g., human). The complex contains a first and second polypeptide. Each of the first and second polypeptides contains at least two similar amino acid sequences at least five amino acid residues in length. In addition, the first and second polypeptides are connected to form the complex, and administration of the complex to the mammal induces an immune response against at least a portion of the first or second polypeptide. The first and/or second polypeptide can contains an amino acid sequence expressed by the mammal. The first and second polypeptides can be identical, and can form a dimer. The connection of the first and second polypeptides can include a disulfide bond. The connection of the first and second polypeptides can include a non-covalent interaction. The first and/or second polypeptide can contain a linker site (e.g., a polyhistidine sequence). The amino and carboxyl termini of the first and/or second polypeptide can contain the linker site. The complex can include a linking molecule (e.g., an antibody such as an anti-polyhistidine antibody). A linking molecule can connects the first and second polypeptide. The complex can contain a third polypeptide, where the third polypeptide has a cytokine activity. The cytokine activity can be an activity of a cytokine such as interferon-α, interferon-β, interferon-γ, TNF-α, IL-1, IL-2, IL-4, IL-6, IL-12, IL-15, IL-18, and granulocyte-macrophage colony stimulating factor. A linking molecule can connect the third polypeptide to the first or second polypeptide. The similar amino acid sequences can be greater than about twenty amino acid residues in length. The complex can contain an Fc-gamma receptor II blocking molecule (e.g., an anti-CD32 antibody).

In another embodiment, the invention features a vaccine complex for vaccinating a mammal (e.g., human). The complex contains a first polypeptide connected to a second polypeptide, where the first polypeptide contains at least two similar amino acid sequences at least five amino acids in length. In addition, the second polypeptide has a cytokine activity, and administration of the complex to the mammal induces an immune response against at least a portion of the first polypeptide. The first polypeptide can contain an amino acid sequence expressed by the mammal. The connection of the first and second polypeptides can include a non-covalent interaction. The first and/or second polypeptide can contain a linker site (e.g., a polyhistidine sequence). For example, the amino and carboxyl termini of the first polypeptide can contain a linker site. The complex can contain a linking molecule (e.g., an antibody such as an anti-polyhistidine antibody). The cytokine activity can be an activity of a cytokine such as interferon-α, interferon-β, interferon-γ, TNF-α, IL-1, IL-2, IL-4, IL-6, IL-12, IL-15, IL-18, and granulocyte-macrophage colony stimulating factor. The complex can contain a third polypeptide. The first and third polypeptides can be identical and can form a dimer. The connection of the first and third polypeptides can include a disulfide bond. The similar amino acid sequences can be greater than about twenty amino acid residues in length. The complex can contain an Fc-gamma receptor II blocking molecule (e.g., an anti-CD32 antibody).

Another embodiment of the invention features a vaccine complex for vaccinating a mammal (e.g., human). The complex contains a first, second, and third polypeptide, where the first, second, and third polypeptides are connected to form the complex. The first polypeptide has a first cytokine activity. The second polypeptide has a second cytokine activity. The administration of the complex to the mammal induces an immune response against at least a portion of the third polypeptide. The third polypeptide can contain an amino acid sequence expressed by the mammal. The connections of the first, second, and third polypeptides can include non-covalent interactions. The first, second, and/or third polypeptide can contain a linker site. The complex can contain a linking molecule. The third polypeptide can contain at least two similar amino acid sequences at least five amino acids in length. The complex can contain an Fc-gamma receptor II blocking molecule (e.g., an anti-CD32 antibody).

Another embodiment of the invention features a vaccine complex for vaccinating a mammal (e.g., human). The complex contains a first polypeptide connected to a second polypeptide, where the first polypeptide is a polypeptide having interferon-α or interferon-β activity, and administration of the complex to the mammal induces an immune response against at least a portion of the second polypeptide. The second polypeptide can contain an amino acid sequence expressed by the mammal. The connection of the first and second polypeptides can include a non-covalent interaction. The first and/or second polypeptide can contain a linker site. The complex can contain a linking molecule. The second polypeptide can contain at least two similar amino acid sequences at least five amino acids in length. The complex can contain an Fc-gamma receptor II blocking molecule (e.g., an anti-CD32 antibody).

Another aspect of the invention features a vaccine for vaccinating a mammal (e.g., human). The vaccine contains an Fc-gamma receptor II blocking molecule (e.g., an anti-CD32 antibody) and a polypeptide, where administration of the vaccine to the mammal induces an immune response against at least a portion of the polypeptide. The polypeptide can contain an amino acid sequence expressed by the mammal. The Fc-gamma receptor II blocking molecule and polypeptide can be connected, and the connection can include a non-covalent interaction.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a diagram comparing the amino acid sequences of the CH2-CH3-CH4 domains of human (SEQ ID NO:1), rat (SEQ ID NO:2), and opossum IgE (SEQ ID NO:3), in the upper, middle, and lower rows, respectively. The opossum sequence also contains an N-terminal signal sequence followed by six histidine residues.

FIGS. 2A–B contain diagrams comparing the amino acid sequences of various polypeptides containing the following components: opossum CH2-rat CH3-opossum CH4 (ORO) (SEQ ID NO:4); opossum CH2-rat N-term CH3-opossum C-term CH3-opossum CH4 (ORO-trunc) (SEQ ID NO:5); opossum CH2-mouse CH3-opossum CH4 (OMO) (SEQ ID NO:6); opossum CH2-CH3-CH4 (OOO) (SEQ ID NO:3); platypus CH2-CH3-CH4 (PPP) (SEQ ID NO:7); opossum CH2-human CH3-opossum CH4 (OHO) (SEQ ID NO:8); opossum CH2-pig CH3-opossum CH4 (OPO) (SEQ ID NO:9); and opossum CH2-dog CH3-opossum CH4 (ODO) (SEQ ID NO:10). The arrows indicate domain borders.

FIGS. 3A–C contain diagrams depicting the analysis of immune responses against an ORO immunogenic polypeptide in a panel of three different strains of rats. The level of rat IgG anti-IgE antibodies directed against native rat IgE was measured by an ELISA. Native rat IgE was used at a concentration of 5 μg/mL for coating of ELISA plates. Successive ⅕ dilutions of serum from each of the individual rats were tested by color reaction in the ELISA. Six vaccinated rats were analyzed together with four control rats from each strain.

FIG. 4 is a diagram depicting an analysis of the immune responses against an ORO immunogenic polypeptide as well as OOO and PPP control polypeptides.

DETAILED DESCRIPTION

The invention provides methods and materials for the treatment of various diseases such as infections and IgE-related diseases. Specifically, the invention provides methods and materials that can be used to vaccinate a mammal against specific self or non-self antigens. For example, the methods and materials described herein can be used to reduce the effects of IgE antibodies within a mammal by reducing the amount of total and receptor bound IgE antibodies in the mammal.

1. Vaccine Conjugates

The invention provides vaccine conjugates that contain at least two polypeptides with each of those polypeptides having at least two similar amino acid segments. The term "conjugate" as used herein refers to any composition containing at least two polypeptides that are directly or indirectly connected via one or more covalent or non-covalent bonds. For example, a conjugate can contain ten sequentially connected polypeptides (e.g., number one is connected to number two, number two is connected to number three, number three is connected to number four, etc.). The term "connected" as used herein with respect to polypeptides refers to any type of covalent or non-covalent bond including, without limitation, single bonds, double bonds, triple bonds, disulfide bonds, hydrogen bonds, hydrophobic interactions, van der Waals interactions, and any combination thereof. For example, a disulfide bond can connect polypeptide number one to polypeptide number two. Alternatively, an antibody can connect polypeptide numbers one and two. In this case, polypeptides one and two each would contain an epitope recognized by the antibody such that the resulting conjugate contains polypeptide number one non-covalently connected to the antibody which is non-covalently connected to polypeptide number two. It is noted that polypeptide numbers one and two in this example can have an identical amino acid sequence.

The term "amino acid segment" as used herein refers to a contiguous stretch of amino acid sequence within a polypeptide. For example, the amino acid sequence from residues 30 to 40 within a 100 amino acid polypeptide would be considered an amino acid segment. For the purpose of this invention, an amino acid segment can be any length greater than about five amino acid residues (e.g., greater than about six, seven, eight, nine, ten, 15, 20, 25, 30, 40, 50, 75, 100, 150, or 200 amino acid residues). Thus, an amino acid segment can be the entire CH3 domain of an IgE antibody.

The term "similar" as used herein with respect to at least two amino acid segments means the segments are at least about 50 percent identical in amino acid sequence. For example, similar amino acid segments can be about 50, 55, 60, 65, 70, 75, 80, 85, 90, 95, 99, or 100 percent identical. For the purpose of this invention, the percent amino acid sequence identity between one amino acid segment and another is calculated as follows. First, the amino acid sequences of the two amino acid segments are aligned using the MEGALIGN® (DNASTAR, Madison, Wis., 1997) sequence alignment software following the Jotun Heim algorithm with the default settings. Second, the number of matched positions between the two aligned amino acid sequences is determined. A matched position refers to a position in which identical residues occur at the same position as aligned by the MEGALIGN® sequence alignment software. Third, the number of matched positions is divided by the total number of positions, and the resulting value multiplied by 100 to obtain the percent identity.

Again, a vaccine conjugate of the invention contains at least two polypeptides with each of those polypeptides having at least two similar amino acid segments. Thus, a vaccine conjugate can contain two, three, four, five, six, seven, eight, nine, ten, 15, 20, 25, or 30 polypeptides with each having at least two similar amino acid segments. It is noted that a polypeptide containing at least two similar amino acid segments can contain two, three, four, five, six, seven, eight, nine, ten, or more similar amino acid segments. In addition to the polypeptides containing at least two similar amino acid segments, a vaccine conjugate of the invention can contain any number of polypeptides not having at least two similar amino acid segments. For example, a vaccine conjugate can contain four polypeptides each having a 30 amino acid residue segment repeated three times as well as two polypeptides each lacking similar amino acid segments.

Typically, a vaccine conjugate contains a polypeptide that will act as an antigen against which an immune response is desired. Thus, a vaccine conjugate within the scope of the invention can contain any type of polypeptide including, without limitation, bacterial polypeptides, fungal polypeptides, viral polypeptides, and mammalian polypeptides. For example, a vaccine conjugate can contain five hepatitis C virus polypeptides. It is noted that each polypeptide of a conjugate can have an identical amino acid sequence. In addition, a polypeptide of a vaccine conjugate typically contains similar amino acid segments each of which can act as a defined antigenic unit against which an immune response is desired. Thus, a polypeptide of a vaccine conjugate can contain similar amino acid segments that correspond to any region from a polypeptide including, without limitation, receptor binding regions, ligand binding regions, enzyme active sites, enzyme cleavage sites of polypeptide substrates, antigen-binding regions of antibodies, and epitopes recognized by antibodies. For example, a polypeptide of a vaccine conjugate can contain three similar amino acid segments that each correspond to the enzyme active site of enzyme X. It is noted that similar amino acid segments can be in tandem or dispersed throughout a polypeptide. Typically, the administration of a vaccine conjugate results in the formation of antibodies having specificity for an epitope formed by at least a portion of the similar amino acid segments within one of the polypeptides of the vaccine conjugate.

Any method can be used to make the polypeptides of a vaccine conjugate including, without limitation, prokaryotic expression systems, eukaryotic expression systems, and chemical synthesis techniques. In addition, a polypeptide of a vaccine conjugate can be obtained from natural tissue sources. For example, a brain glycopolypeptide can be obtained from brain tissue. Typically, each different polypeptide of a conjugate is made independently, or isolated independently, and then used to form a conjugate. It is noted that polypeptides can be purified prior to being used to form a conjugate. Any method can be used to purify polypeptides including, without limitation, fractionation, centrifugation, and chromatography. For example, polypeptides containing a polyhistidine sequence can be purified using affinity chromatography. Once obtained, the polypeptides can be connected using any method. For example, a polypeptide sample can be incubated with a linking molecule such that individual polypeptides form conjugates. A linking molecule is any molecule that connects two polypeptides. Typically, a linking molecule is a molecule with two reactive groups or sites that are capable of interacting with and thereby forming a link between amino acid residues from two polypeptides. A linking molecule can be a specific linking molecule such as an antibody or a non-specific linking molecule such as a chemical reagent (e.g., glutaraldehyde and formaldehyde).

Any antibody can be used as a linking molecule. For example, an anti-polyhistidine antibody or an anti-epitope tag antibody such as an anti-FLAG® epitope antibody or anti-hemagglutinin (HA) tag antibody can be used to connect two polypeptides. FLAG® epitopes are described in U.S. Pat. Nos. 4,703,004 and 4,782,137. It is noted that the polypeptides to be connected with a specific linking molecule need to contain the specific site recognized by the linking molecule. For example, to connect two polypeptides with an anti-polyhistidine antibody, each polypeptide must contain the polyhistidine epitope recognized by that antibody. For the purpose of this invention, the specific site recognized by a specific linking molecule such as an antibody is referred to as a linker site. Any method can be used to make a polypeptide that contains a linker site such that a particular antibody can be used as a linking molecule. For example, common molecular cloning techniques can be used to introduce the nucleic acid that encodes a FLAG tag epitope into the nucleic acid that encodes a particular polypeptide. It is noted that a linker site can be located at any position. For example, a polyhistidine sequence can be at the N-terminus, C-terminus, or an internal position of a polypeptide. In addition, a polypeptide can contain more than one linker site. For example, a polypeptide can have a polyhistidine sequence at an internal position as well as at the C-terminus. Further, a polypeptide can contain different linker sites. For example, a polypeptide can have a polyhistidine sequence at an internal position and a FLAG tag epitope at the C-terminus.

In some cases, two or more polypeptides can be made such that they are connected via a covalent bond. For example, two polypeptides can be made as a fusion protein such that they are connected by a peptide bond. Alternatively, a polypeptide can be made in a cell line that promotes the formation of disulfide bonds between, for example, two identical polypeptides. In this case, the conjugate would be a homodimer. It is noted that any polypeptide can be engineered to contain one or more cysteine residues such that the polypeptides form conjugates via cysteine bridges. For example, a polypeptide can be made to contain N- and C-terminal cysteine residues such that conjugates of varying size are formed intracellularly.

In addition, the interaction between biotin and avidin can be used to form conjugates. For example, polypeptides can be designed, or chemically treated, to contain biotin molecules at the C- and N-terminal ends. These biotin-containing polypeptide can be incubated with avidin molecules that are capable of simultaneously interacting with two or more biotin molecules. In this case, a single avidin molecule can link two biotin-containing polypeptides to form a conjugate. Further, chelating molecules that can simultaneously bind two or more ions (e.g., $Ni^{++}$, $Cu^{++}$, $Co^{++}$, and $Zn^{++}$) can be used to form conjugates. For example, a copper chelating molecule that can interact with two copper ions can be used to link two polypeptides containing a polyhistidine sequence. In this case, a single copper ion can interact with each polyhistidine sequence while a single copper chelating molecule links the two polypeptides to form a conjugate. It is noted that immunostimulating complexes (iscoms) can be used to form conjugates. For example, an iscom can be designed to contain copper ions such that polypeptides containing a polyhistidine sequence can be conjugated.

Typically, a nucleic acid molecule is constructed such that a particular polypeptide is expressed. For example, a nucleic acid molecule can be constructed to encode a polypeptide having three similar amino acid segments as well as a polyhistidine sequence at its C-terminus. Once constructed, the nucleic acid molecule can be introduced into a host cell such that the polypeptide is produced. Any host cell can be used including, without limitation, prokaryotic cells (e.g., bacteria) and eukaryotic cells (e.g., human cells). Once produced, the polypeptide can be purified and used to make the desired vaccine conjugate.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

Nucleic acid can be obtained using common molecular cloning or chemical nucleic acid synthesis procedures and techniques, including PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Any method can be used to introduce nucleic acid into a cell. In fact, many methods for introducing nucleic acid into cells, whether in vivo or in vitro, are well known to those skilled in the art. For example, calcium phosphate precipitation, electroporation, heat shock, lipofection, microinjection, and viral-mediated nucleic acid transfer are common methods for introducing nucleic acid into cells. In addition, naked DNA can be delivered directly to cells in vivo as describe elsewhere (U.S. Pat. No. 5,580,859 and U.S. Pat. No. 5,589,466 including continuations thereof). Further, nucleic acid can be introduced into cells by generating transgenic animals. It is noted that transgenic animals such as rabbits, goats, sheep, and cows can be engineered such that large amounts of a polypeptide are secreted into their milk.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce nucleic acid into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA,* 82:6148–6152 (1985)); gene transfection into embryonic stem cells (Gossler A et al., *Proc Natl Acad Sci USA* 83:9065–9069 (1986)); gene targeting into embryonic stem cells (Thompson et al., *Cell,* 56:313–321 (1989)); nuclear transfer of somatic nuclei (Schnieke A E et al., *Science* 278:2130–2133 (1997)); and electroporation of embryos.

For a review of techniques that can be used to generate and assess transgenic animals, skilled artisans can consult Gordon (*Intl. Rev. Cytol,* 115:171–229 (1989)), and may obtain additional guidance from, for example: Hogan et al., "Manipulating the Mouse Embryo" Cold Spring Harbor Press, Cold Spring Harbor, N.Y. (1986); Krimpenfort et al., *Bio/Technology,* 9:844–847 (1991); Palmiter et al., *Cell,* 41.343–345 (1985); Kraemer et al., "Genetic Manipulation of the Early Mammalian Embryo" Cold Spring Harbor Press, Cold Spring Harbor, N.Y. (1985); Hammer et al., *Nature,* 315:680–683 (1985); Purscel et al., *Science,* 244:1281–1288 (1986); Wagner et al., U.S. Pat. No. 5,175, 385; and Krimpenfort et al., U.S. Pat. No. 5,175,384.

In addition, a nucleic acid that encodes a polypeptide can be maintained within a cell in any form. For example, nucleic acid can be integrated into the genome of a cell or maintained in an episomal state. In other words, a cell can be a stable or transient transformant.

Further, any method can be used to direct the expression of a particular polypeptide. Such methods include, without limitation, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like.

In one embodiment, a conjugate to vaccinate rats can be designed to contain polypeptides having an N-terminal polyhistidine sequence followed by an opossum IgE CH2 domain, a rat IgE CH3 domain, an opossum IgE CH2 domain, a rat IgE CH3 domain, an opossum IgE CH4 domain, and a C-terminal polyhistidine sequence. Alternatively, the first opossum IgE CH2 domain can be followed by three rat IgE CH3 domains as opposed to only one rat IgE CH3 domain. In either case, two polypeptides can be connected via disulfide bonds such that dimers are formed. It is noted that affinity chromatography can be used to purify polypeptides containing a polyhistidine sequence. In addition, an anti-polyhistidine antibody can be used as a linking molecule to connect any number of single polypeptides or dimers through the N-terminal and C-terminal polyhistidine sequences. For example, three dimers can be linked sequentially via two anti-polyhistidine antibodies (i.e., dimer one connected to dimer two by antibody one, and dimer two connected to dimer three by antibody two). It is noted that mixing polypeptides with a linking molecule can result in a vaccine that contains vaccine conjugates with various sizes as well as various combinations of polypeptides. For example, a vaccine can contain a substantial amount of vaccine conjugates having less than four polypeptides with few having greater than four polypeptides. It is also noted that the general configuration of the polypeptides within a vaccine conjugate can be adapted to vaccinate mammals other than rats. For example, the rat IgE domains can be replaced with human IgE domains to vaccinate humans.

2. Vaccine Conjugates and Cytokines

The invention provides vaccine conjugates that contain a polypeptide having a cytokine activity such that a potent immune response is induced against another polypeptide within the conjugate. Such immune responses can be more potent than the responses induced by a conjugate lacking a polypeptide having a cytokine activity. Although not limited to any particular mode of action, a vaccine conjugate containing polypeptide X and a polypeptide having a cytokine activity presumably concentrates cytokine activity to the localized area containing polypeptide X. Thus, a vaccine conjugate containing a polypeptide having cytokine activity can stimulate cells that participate in generating a specific immune response against other polypeptides within a vaccine conjugate.

A polypeptide having cytokine activity can have any type of cytokine activity. For example, a polypeptide can have interferon-α, interferon-β, interferon-γ, TNF-α, IL-1, IL-2, IL-4, IL-6, IL-12, IL-15, IL-18, or granulocyte-macrophage colony stimulating factor (GM-CSF) activity. It is important to note that a polypeptide having cytokine activity can be a polypeptide that is either naturally occurring or non-naturally occurring. A naturally occurring polypeptide is any polypeptide having an amino acid sequence as found in nature, including wild-type and polymorphic polypeptides. Such naturally occurring polypeptides can be obtained from any species including, without limitation, human, chimpanzee, baboon, rat, or mouse. For example, human interferon-α can be used in a vaccine conjugate. A non-naturally occurring polypeptide is any polypeptide having an amino acid sequence that is not found in nature. Thus, a non-naturally occurring polypeptide can be a mutated version of a naturally occurring polypeptide, or an engineered polypeptide. For example, a non-naturally occurring polypeptide having interferon-α activity can be a mutated version of a naturally occurring polypeptide having interferon-α activity that retains at least some interferon-α activity. A polypeptide can be mutated by, for example, sequence additions, deletions, and/or substitutions using standard methods such as site-directed mutagenesis of the corresponding nucleic acid coding sequence.

A conjugate can contain any number of polypeptides having cytokine activity. For example, a conjugate can contain two polypeptides having cytokine activity. In addition, a conjugate can contain polypeptides having different cytokine activities. For example, a conjugate can contain one polypeptide having interferon-α activity and another having GM-CSF activity. It is noted that polypeptides having cytokine activity can be obtained using any method. For example, a polypeptide having cytokine activity can be designed to contain a polyhistidine sequence such that affinity chromatography can be used to purify the polypeptide. In addition, any method can be used to form a conjugate. For example, a polypeptide having cytokine activity can be designed to contain a linker site such that a linking molecule can link that polypeptide to another polypeptide such as any of the polypeptides described herein.

In one embodiment, a conjugate to vaccinate rats can be designed to contain polypeptides having cytokine activity as well as polypeptides having an N-terminal polyhistidine sequence followed by an opossum IgE CH2 domain, a rat IgE CH3 domain, an opossum IgE CH2 domain, a rat IgE CH3 domain, an opossum IgE CH4 domain, and a C-terminal polyhistidine sequence. In this case, the polypeptides having cytokine activity can contain an N-terminal polyhistidine sequence such that affinity chromatography can be used for purification. In addition, an anti-polyhistidine antibody can be used as a linking molecule to connect any number of polypeptides via the polyhistidine sequences. For example, a conjugate can contain an interferon-α polypeptide followed by three polypeptides containing IgE domains followed be an interferon-β polypeptide with each connection being via an anti-polyhistidine antibody. It is noted that mixing polypeptides with a linking molecule can result in a vaccine that contains vaccine conjugates with various sizes and various combinations of polypeptides. For example, a vaccine can contain a substantial amount of vaccine conjugates having polypeptides with interferon-α activity with few having both polypeptides with interferon-α activity and polypeptides with interferon-β activity. It is also noted that the general configuration of the polypeptides within a vaccine conjugate can be adapted to vaccinate mammals other than rats. For example, the rat IgE domains can be replaced with human IgE domains to vaccinate humans.

3. Immunogenic Polypeptides and IgE Vaccines

For a successful IgE vaccination, it is essential to obtain a strong immune response that reacts predominantly with native IgE molecules (e.g., IgE surface epitopes). This is required in order to achieve efficient competition with the IgE receptor for free IgE, as the interaction between an IgE antibody and its specific IgE receptor is very strong ($2.6\times 10^{-10}$; Froese A, *CRC Crit. Rev. Immunol.* 1:79–132 (1980)). As described herein, high levels of antibodies having specificity for self IgE antibodies were produced in rat strains by administering an immunogenic polypeptide. Several different rat strains were used including low, medium, and high IgE responders.

An immunogenic polypeptide, as described herein, is a polypeptide that effectively induces an immune response in a mammal. For example, an immunogenic polypeptide can be a polypeptide that effectively induces an anti-self IgE response in a mammal. Typically, immunogenic polypeptides contain at least one amino acid sequence (e.g., a single amino acid substitution) that would be considered non-self to a particular mammal. For example, immunogenic polypeptides that induce anti-self IgE responses can contain two components: a self IgE portion and a non-self IgE portion. The self IgE portion can be responsible for conferring the specificity of the anti-self IgE response and the non-self IgE portion can serve to promote and stabilize the immunogenic polypeptide such that the specific anti-self IgE response is induced. Typically, the self IgE portion of the immunogenic polypeptide is a portion of an IgE antibody that either directly interacts with an IgE receptor or indirectly influences the interaction of an IgE antibody with an IgE receptor.

Briefly, the binding site for human IgE to the high affinity IgE receptor on mast cells and basophils is not located at the junction between the CH2 and CH3 domains of IgE as previously suggested, but instead is located in the N-terminal region of the CH3 domain. This region is, due to folding, located in the junction between the CH3 and CH4 domains of the native polypeptide. Thus, use of the entire CH2-CH3 domain as a self IgE portion may potentially induce an anti-self IgE response with antibodies interacting with self IgE antibodies already bound to the surface of mast cells such that anaphylactic reactions occur. To reduce the risk of inducing an anaphylactic response, the self IgE portion of an immunogenic polypeptide can be the entire CH3 domain without the CH2 domain. Alternatively, the self IgE portion can be the N-terminal region of the CH3 domain. For example, when vaccinating a rat, the self IgE portion can be the N-terminal half of the rat CH3 domain in a context of a non-self IgE portion containing the entire CH2 domain of opossum IgE, the C-terminal half of the CH3 domain of opossum IgE, and the entire CH4 domain of opossum IgE. Such an immunogenic polypeptide can be designated ORO-trunc (FIG. 2).

Typically, the non-self IgE portion of an immunogenic polypeptide stabilizes a functional conformation of the self IgE portion. For example, if the self IgE portion is a CH3 domain, then the non-self IgE portion could be a CH2 domain, a CH4 domain, or a CH2 and CH4 domain with the self CH3 domain being between the CH2 and CH4 domains. Specifically, when vaccinating a rat, the self IgE portion can be the rat CH3 domain in a context of a non-self IgE portion from, for example, opossum. In this case, the rat CH3 domain can be located between the opossum CH2 and CH4 domains. Such an immunogenic polypeptide can be designated ORO (FIG. 2). Likewise, when vaccinating a mouse, the self IgE portion can be the mouse CH3 domain in a context of a non-self IgE portion from, for example, opossum. Such an immunogenic polypeptide can be designated OMO (FIG. 2).

Immunogenic polypeptides of the invention can be produced using a eukaryotic expression system, such as a mammalian cell expression system. In such cases, the immunogenic polypeptide is soluble, properly folded, and properly modified such that an anti-self IgE response is induced upon administration to a mammal. For example, immunogenic polypeptides having one or more eukaryotic post-translational modifications can produce an anti-self IgE response that is significantly higher than similar polypeptides lacking eukaryotic post-translational modification (e.g., a bacterially produced polypeptide). Eukaryotic post-translational modifications include, without limitation, glycosylation, acylation, limited proteolysis, phosphorylation, and isoprenylation. Further, soluble, properly folded, and properly modified immunogenic polypeptides can induce a strong anti-self IgE response in mammals with high concentrations of plasma IgE, so called high IgE responders. Bacterially produced polypeptides, however, are unable to produce such a strong anti-self IgE response in high IgE responders. Thus, immunogenic polypeptides having high solubility, proper folding, and proper modification can be obtained and used as described herein to induce effective anti-self IgE responses in mammals. Moreover, the immunogenic polypeptides described herein can be used to treat mammals, including humans, that have high serum concentrations of IgE. It is noted that a high percentage of the severely allergic patients in the human population belong to this category of patients.

The IgE CH3 domain, or a portion of an IgE CH3 domain, derived from an organism to be vaccinated such as human can be inserted into the structural context of a distantly related IgE molecule such as an IgE molecule from a non-placental mammal (e.g., opossum, platypus, koala, kangaroo, wallaby, and wombat). IgE antibodies from the grey short tailed opossum, a marsupial, exhibit about 25 percent sequence identity with human, rat, pig, and dog IgE antibodies. Thus, regions of the opossum IgE antibody can be used as the non-self IgE portion of an immunogenic polypeptide such that a potent anti-self IgE response is induced in a human, rat, pig, or dog.

A nucleic acid molecule for expressing an immunogenic polypeptide can be produced by splicing a first nucleic acid that encodes a portion of an IgE antibody from an organism to be vaccinated into a second nucleic acid that encodes a portion of an IgE antibody from a mammal distantly related to the organism to be vaccinated. For example, a nucleic acid molecule encoding an immunogenic polypeptide containing the CH3 domain of rat, human, pig, or dog IgE can be spliced into a nucleic acid containing the CH2 and CH4 domains of opossum IgE. Such chimeric nucleic acid molecules can be constructed using common molecular cloning techniques. In general, constructing nucleic acid such that the CH3 domain of an IgE antibody from one organism is positioned between the CH2 and CH4 domains of an IgE antibody from another organism results in a nucleic acid molecule that encodes a chimeric IgE molecule that has the CH3 domain in a structural context very similar to its native position within native IgE antibodies.

When vaccinating rat, human, dog, or pig, the opossum CH2 and CH4 domains can serve as the non-self IgE portion of the immunogenic polypeptide, since there is about 30 percent amino acid identity between opossum CH2 and CH4 domains and the corresponding domains of rat, human, dog, and pig IgE (FIG. 1). Such immunogenic polypeptides can be produced in a mammalian host. In addition, the resulting immunogenic polypeptides can be secreted from the mammalian producer cells in a properly folded and properly glycosylated form. For example, analysis, in the Biacore system, with monoclonal antibodies directed against the CH3 domain of human IgE revealed that these monoclonal antibodies can bind strongly to immunogenic polypeptides of the invention, indicating that the entire CH3 domain can be properly folded.

It is important to note that immunogenic polypeptides described herein can be such that deleterious side-effects are not exhibited, even in mammals that have highly elevated IgE titres prior to vaccination. In addition, vaccination with an immunogenic polypeptide as described herein can induce an anti-self IgE response that is directed against the entire free pool of IgE. Such a response is not limited to a specific allergen. Thus, these methods and materials can be used to treat human allergies having a large variety of different atopic allergies.

4. Additional Components and Modes of Administration

The vaccines, vaccine conjugates, and immunogenic polypeptides described herein can be administered alone or in combination with other components. For example, a vaccine conjugate can contain a blocking molecule that inhibits the interaction between an antibody (e.g., an IgG antibody) and an Fc-gamma receptor II (e.g., CD32). Such blocking molecules (i.e., Fc-gamma receptor II blocking molecules) can include, without limitation, anti-CD32 antibodies. Anti-CD32 antibodies can be obtained using common antibody production and screening techniques. It is noted that Fc-gamma receptor II blocking molecules can be used in combination with any immunogenic polypeptide such that the immune response against the immunogenic polypeptide is enhanced. For example, a mixture containing an anti-CD32 antibody and an immunogenic polypeptide either conjugated or not can be administered to a mammal to induce a potent immune response against the immunogenic polypeptide.

To vaccinate a mammal, an effective amount of any vaccine, vaccine conjugate, or immunogenic polypeptide described herein can be administered to a host. An effective amount refers to any amount that induces a desired immune response while not inducing significant toxicity to the host. Such an amount can be determined by assessing a host's immune response after administration of a fixed amount of a particular material (e.g., immunization polypeptide). In addition, the level of toxicity, if any, can be determined by assessing a host's clinical symptoms before and after administering a fixed amount of a particular material. It is noted that the effective amount of a particular material administered to a host can be adjusted according to desired outcomes as well as the host's response and level of toxicity. Significant toxicity can vary for each particular host and depends on multiple factors including, without limitation, the host's disease state, age, and tolerance to pain.

In addition, any of the materials described herein can be administered to any part of the host's body including, without limitation, the joints, blood stream, lungs, intestines, muscle tissues, skin, and peritoneal cavity. Thus, a vaccine conjugate can be administered by intravenous, intraperitoneal, intramuscular, subcutaneous, intrathecal, and intradermal injection, by oral administration, by inhalation, or by gradual perfusion over time. For example, an aerosol preparation containing an immunogenic polypeptide can be given to a host by inhalation. It is noted that the duration of vaccination with any of the materials described herein can be any length of time from as short as one day to as long as a lifetime (e.g., many years). For example, an immunogenic polypeptide can be administered once a year over a period of ten years. It is also noted that the frequency of treatment can be variable. For example, an immunogenic polypeptide can be administered once (or twice, three times, etc.) daily, weekly, monthly, or yearly.

Preparations for administration can include sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water as well as alcohol, saline, and buffered solutions. Preservatives, flavorings, and other additives such as, for example, anti-microbials, anti-oxidants, chelating agents, inert gases, and the like may also be present. It will be appreciated that any material described herein that is to be administered to a mammal can contain one or more commonly known pharmaceutically acceptable carriers.

Any method can be used to determine if a particular immune response is induced. For example, antibody responses against particular antigens can be determined using immunological assays (e.g., ELISA). In addition, clinical methods that can assess the degree of a particular disease state can be used to determine if a desired immune response is induced.

The invention will be further described in the following examples, which do not limit the scope of the invention described in the claims.

EXAMPLES

Example 1

Immunogenic Polypeptides

Nucleic acid molecules were constructed to encode immunogenic polypeptides containing both self and non-self IgE portions. These nucleic acid molecules were then used to synthesize soluble immunogenic polypeptides in mammalian cells. Such immunogenic polypeptides effectively induced a polyclonal anti-self IgE response upon administration to a mammal. In addition, the immunogenic polypeptides appear to be folded and glycosylated in a manner that enabled the immunogenic polypeptides to produce a strong and specific anti-self IgE response that was more potent than bacterially produced polypeptides lacking the non-self IgE portion. Thus, the immunogenic polypeptides described herein contain a majority of the surface epitopes in the same conformation as in native plasma IgE. Moreover, immunogenic polypeptides containing a self IgE portion limited to either the entire CH3 domain or a fragment of the CH3 domain (e.g., N-terminal region of CH3) reduced the potential of producing anaphylactic antibodies within a mammal.

Example 2

Production and Purification of an Immunogenic Polypeptide

A ~330 base pair PCR fragment encoding the CH3 domain of rat IgE (Hellman L et al., *Nucleic Acids Res.* 10:6041–6049 (1982)) was fused with two similar sized fragments encoding the CH2 and CH4 domains of opossum IgE (Aveskogh M and Hellman L, *Eur. J. Immunol.*, 28:2738–2750 (1998)) by ligation into a modified version of the pCEP4 expression vector, pCEP-Pu2 (Margolskee R F et al., *Mol. Cell Biol.* 8:2837–2847 (1988)). This vector contains the CMV promoter-enhancer, located directly 5' of the coding region of interest and allows high levels of expression in mammalian cells. This vector also contains the coding regions for puromycin resistance and the EBV EBNA1 gene. The EBNA1 gene confers maintenance of stable replicating episomal copies of the vector in human or canine cell lines.

The nucleic acid molecule containing the opossum IgE CH2, rat IgE CH3, and opossum IgE CH4 nucleic acid sequences also contained nucleic acid sequences that encode a signal sequence and six histidine residues at the N-terminal region. The region containing the signal sequence and six histidine residues facilitates secretion of the encoded polypeptide from producer cells and enables polypeptide purification with $Ni^{++}$-chelating columns. Following transfection of the expression vector into human 293 cells, the opossum CH2-IgE/rat CH3-IgE/opossum CH4-IgE (ORO) immunogenic polypeptide was purified from 293 cell conditioned media on a nickel-chelating column to about 100 percent purity. Following elution of the ORO immunogenic polypeptide with a solution containing 20 mM Tris (pH 8.0), 0.1 M NaCl, and 100 mM imidazole, the eluate was dialyzed against PBS (pH 7.5) overnight at 4° C. The ORO immunogenic polypeptide was then concentrated to about 2 mg/mL using an Amicon concentrator. An aliquot of this preparation containing the ORO immunogenic polypeptide was separated on SDS-PAGE and found to be about 100 percent pure. This purified ORO immunogenic polypeptide preparation was used as the active component of an anti-self IgE vaccine for treating rats.

Example 3

Sensitization Procedure

Each rat was sensitized to ovalbumin as follows. Ten (10) μg of ovalbumin in PBS was administered to each rat intraperitoneally. Three weeks after this initial intraperitoneal injection of ovalbumin, the rats received weekly intraperitoneal injections of 1 μg of ovalbumin for four weeks. During this four week period, the rats became sensitized to ovalbumin obtaining a total IgE and ovalbumin-specific IgE response that was high and persistent. After this four week period, the rats started a vaccination program. During the entire vaccination program, intraperitoneal injections of ovalbumin continued as follows. During the first two weeks of vaccination, the rats received intraperitoneal injections of 1 µg of ovalbumin weekly. After the first two weeks of vaccination, the rats received intraperitoneal injections of 1 µg of ovalbumin every other week.

Example 4

ELISA Measurement of an Anti-self IgE Response

Thirty-six rats (twelve Lewis rats, twelve Louvain rats, and twelve Brown Norway rats) were divided into two equally sized groups and injected intraperitoneally with either the ORO immunogenic polypeptide or BSA as negative control. The BSA negative control was used at the same polypeptide concentration as that of the ORO immunogenic polypeptide. In this study, each rat received intraperitoneal injections of about 250 µg of antigen (either the ORO immunogenic polypeptide or BSA) dispersed in 0.2 mL of a 50:50 solution of Freund's complete adjuvant and PBS. Three weeks later, the rats were given a booster injection containing about 100 µg of antigen dispersed in 0.1 mL of a 50:50 solution of Freund's incomplete adjuvant and PBS. Six weeks later, the rats were given an additional booster identical to the first booster. One week after this third immunization, blood samples were taken and measured in an ELISA as follows.

The level of IgG anti-IgE antibodies directed against self rat IgE was measured by an ELISA. Native rat IgE was used at a concentration of 5 µg/mL for coating the ELISA plates. Successive ⅕ dilutions of serum from each of the individual rats were tested by color reaction in the ELISA. The presence of rat IgG antibodies having specificity for rat IgE antibodies was determined using two biotinylated mouse monoclonal antibodies, one with specificity for rat IgG2a/b and one for rat IgG1. Alkaline phosphatase coupled strepavidin was used to detect these biotinylated mouse monoclonal antibodies.

Example 5

Induction of an Anti-self IgE Response in a Mammal

Figure 3B:
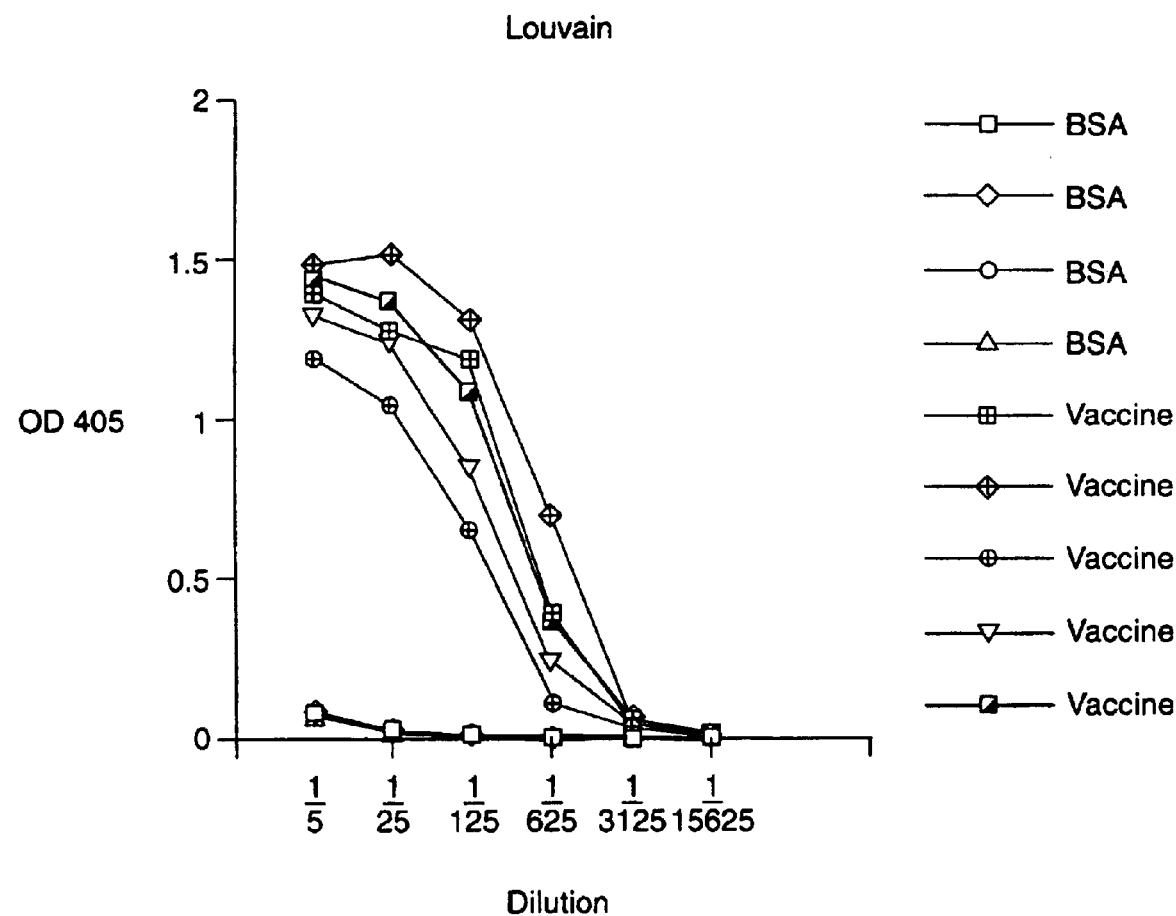
Figure 3C:
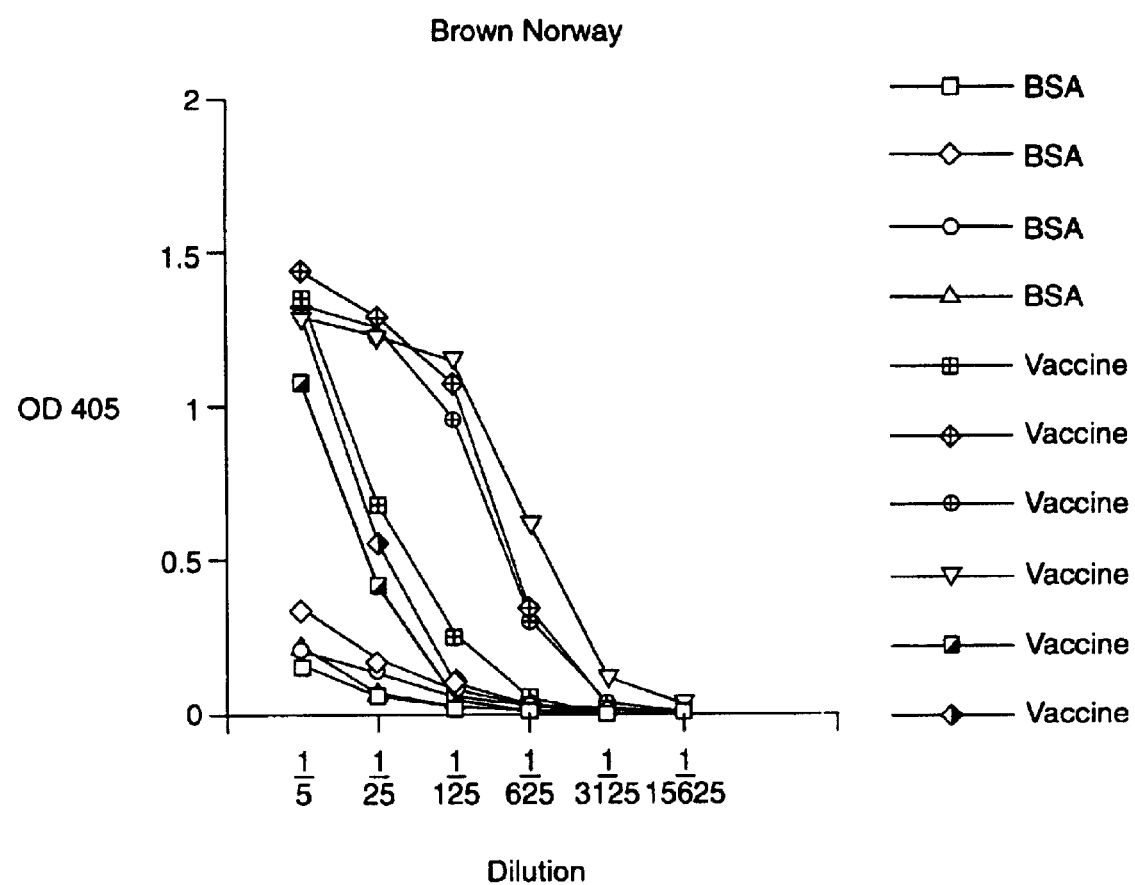

The in vivo effect of the ORO immunogenic polypeptide as an IgE vaccine was investigated using three different strains of rats (Lewis, Louvain, and Brown Norway). Lewis rats are low IgE responders, Louvain rats are medium IgE responders, and Brown Norway rats are high IgE responders. After sensitization to ovalbumin, each rat was vaccinated with either the ORO immunogenic polypeptide or BSA as described in Example 3. After collecting blood samples, the sera was diluted in steps of five as indicated (FIG. 3). Purified monoclonal rat IgE (IR 162) was used to coat the ELISA plates (5 µg/mL) and two biotinylated mouse monoclonal antibodies were used to detect rat IgG anti-IgE antibodies. Following the second booster dose, high anti-IgE titres were detected in the low, medium, and high IgE responding rats that received the vaccine containing the ORO immunogenic polypeptide. Anti-IgE titers were not detected in rats treated with the BSA control. Thus, the ORO immunogenic polypeptide was capable of inducing an anti-self IgE response in rats that contained low, medium, and high amounts of IgE antibodies.

A difference in anti-self IgE levels between the various strains was observed. The low responder strain, Lewis, showed very high anti-self IgE titres. The sera could be diluted more than 3000 times before a significant decrease in OD values upon ELISA measurements was detected (FIG. 3). For the high responder strain, Brown Norway, however, the OD values started to drop for three out of six animals at a dilution of 25 times or more (FIG. 3).

In another experiment, Wistar rats were used. Wistar rats are medium IgE responders. The anti-self IgE response produced by the Wistar rats was similar to the response observed in the Lewis rats.

Example 6

Analysis of Cross Reactivity

The cross reactivity between rat antibodies directed against an opossum IgE CH2 or CH4 domain with the corresponding domain of rat IgE antibodies was evaluated. This potential cross reactivity could result from a low primary amino acid sequence homology or a close structural similarity between the CH2 and CH4 domains of opossum IgE and rat IgE. The induction of an anti-rat IgE response having specificity for the rat CH2 or CH4 domains could lead to mast cell activation.

Figure 4:
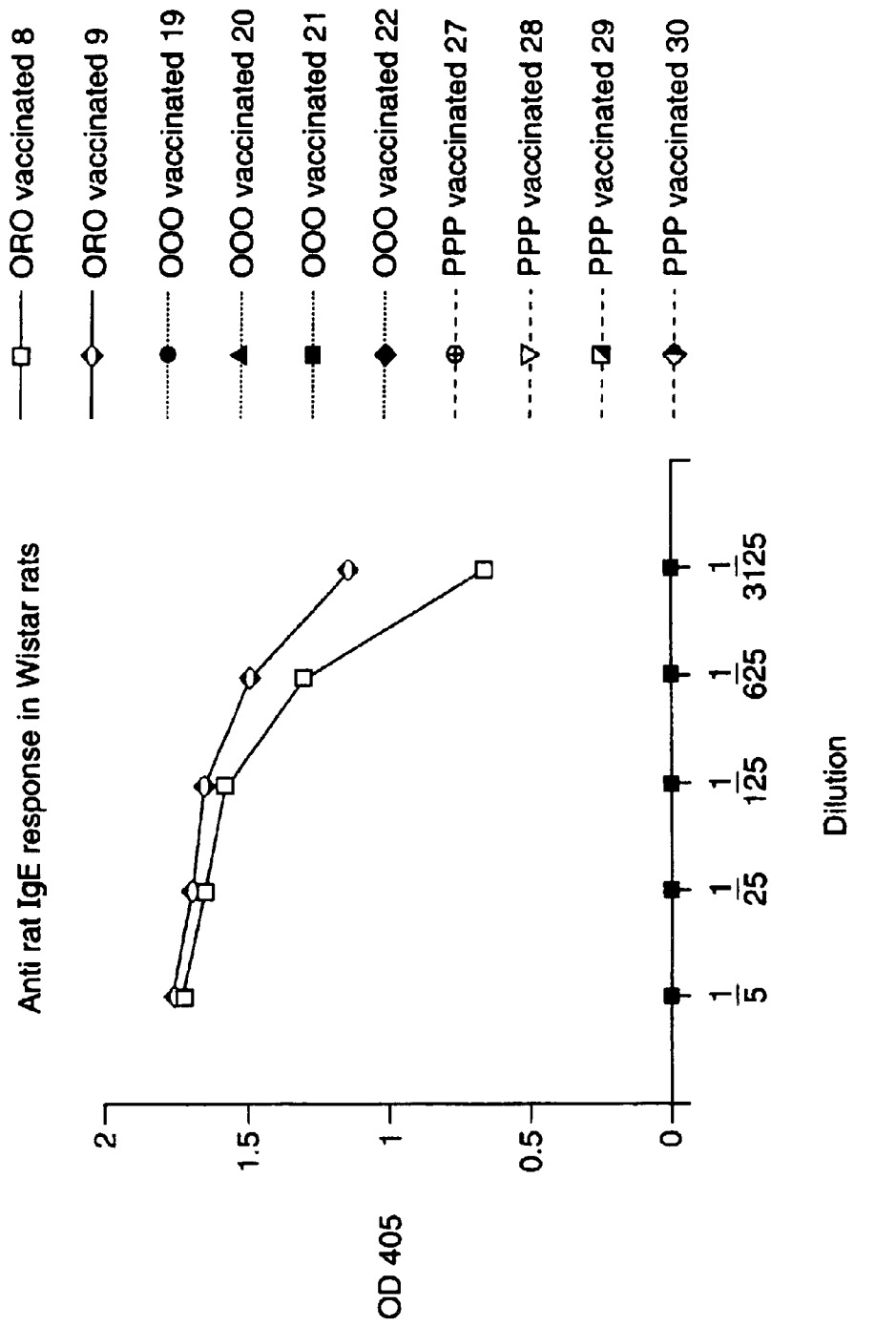

A recombinant polypeptide (OOO) containing the opossum CH2-CH3-CH4 domains was injected into the Wistar strain. After a second booster injection, sera from these rats were collected and tested for the presence of antibodies having specificity for rat IgE. No anti-rat IgE antibodies were detected in the rats treated with the OOO polypeptide (FIG. 4). In addition, Wistar rats treated with the ORO immunogenic polypeptide exhibited an anti-self IgE response similar to that observed in Lewis rats. Further, Wistar rats treated with a recombinant polypeptide (PPP) containing platypus CH2-CH3-CH4 domains did not produce an anti-rat IgE response. Thus, the CH2, CH3, and CH4 domains of opossum and platypus IgE antibodies do not generate, upon administration to rats, rat antibodies having specificity for rat IgE antibodies.

The interaction between the rat antibodies induced by the ORO immunogenic polypeptide (rat IgG anti-self IgE antibodies) and human IgE antibodies was examined. In a few cases, minor cross reactivity was observed. This minor cross reactivity detected in a few rats was most likely caused by the interaction between rat IgG anti-rat CH3 IgE antibodies and the CH3 domain of human IgE. Since the CH3 domains of rat and human IgE are much more closely related than human and opossum or platypus IgE, vaccines containing opossum or platypus components can be considered highly safe, presenting minimal risk for the generation of cross linking antibodies.

Example 7

Polypeptides for Vaccine Conjugates

The nucleic acid construct encoding the ORO immunogenic polypeptide described in Example 2 was used to produce two polypeptides each having several identical self epitopes. One polypeptide contained two identical clusters of self epitopes (the entire rat CH3 domain), while the other polypeptide contained four such clusters. First, nucleic acid encoding six histidine residues was added to the C-terminal end of the opossum CH4 domain by including a nucleotide sequence for six histidine residues in the 3' PCR primer. Thus, each polypeptide contained a polyhistidine sequence at both the N- and C-terminal ends so that conjugates can be formed. Second, a nucleic acid fragment encoding the opossum CH2 and the rat CH3 domains of the original construct was obtained by PCR amplification. This fragment was subsequently ligated into the construct encoding the ORO immunogenic polypeptide. The resulting construct encoded a polypeptide designated ORORO. This ORORO polypeptide contains two rat CH3 domains, two opossum CH2 domains, and one opossum CH4 domain in the following order opossum CH2, rat CH3, opossum CH2, rat CH3, and opossum CH4. Thus, this polypeptide has two identical CH3 domains, each with multiple self epitopes.

The nucleic acid construct encoding ORORO was used as starting material to produce the second immunogenic polypeptide. This polypeptide contains two additional rat CH3 domains that were added to a position 3' of the first rat CH3 domain in the ORORO polypeptide. The resulting polypeptide has a polyhistidine tag followed by an opossum CH2 domain, three identical rat CH3 domains, one opossum CH2 domain, one rat CH3 domain, an opossum CH4 domain, and a C-terminal polyhistidine tag (6his-ORRRORO-6his).

Each recombinant polypeptide was produced in the pCEP4 based vector system. In addition, the polypeptides were purified using $Ni^{++}$ chelating columns according to the method described in Example 2. Similar vaccine constructs are produced using dog or human IgE CH3 domain instead of the rat IgE CH3 domain.

Example 8

Vaccine Conjugates

To determine a favorable combination of polypeptide to monoclonal antibody, the purified polypeptides of Example 7 are mixed with a monoclonal anti-polyhistidine antibody in various combinations ranging from a 1/1 to a 10/1 ratio (polypeptide to monoclonal antibody ratio). This mixture results in the generation of long multimeric conjugates with a large number of identical self epitopes in tandem. The biological activity of the various combinations is assessed in rats as described herein. The non-conjugated ORO immunogenic polypeptide is used as a reference to assess immune responses.

Example 9

Polypeptides having Cytokine Activity

PCR primers are designed so that cDNAs encoding rat, dog, and human cytokines (e.g., interferon-α, interferon-γ, and GM-CSF) can be isolated from total spleen mRNA. The nucleotide sequence encoding six histidine residues is introduced into each 5' PCR primer so that the cytokines can be purified via affinity chromatography and can be non-covalently conjugated to the polypeptides described herein via an anti-polyhistidine antibody. The recombinant cytokines are produced using any one of the following three expression systems: bacteria, yeast (e.g., *Pichia pastoris*), and mammalian cells (e.g., 293-EBNA cells using a pCEP-4 based expression system).

Example 10

Vaccine Conjugates having a Polypeptide With Cytokine Activity

Cytokines produced according to Example 9 are used to make vaccine conjugates. A mixture of three different cytokines (e.g., mouse interferon-α, rat interferon-γ and rat GM-CSF) is produced and tested in combination with the ORORO polypeptide and an anti-polyhistidine antibody.

Initially, a mixture of 1/10 ratio (cytokine to immunogenic polypeptide ratio) is tested. With three cytokines, this ratio results in a mixture of 30% cytokine per molar basis and 70% immunogenic polypeptide. In addition, this mixture contains an anti-polyhistidine antibody at a 1/10 ratio (immunogenic polypeptide to monoclonal antibody ratio). A large number of ratio combinations is evaluated so that an optimal cytokine to immunogenic polypeptide ratio as well as an optimal monoclonal antibody to immunogenic polypeptide ratio is determined. In addition, polypeptides having cytokine activity from various species is assessed to determine the optimal combination for a particular species.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An immunogenic polypeptide comprising a human IgE CH3 domain located between an opossum IgE CH2 domain and an opossum IgE CH4 domain wherein said immunogenic polypeptide is effective to induce an anti-human IgE response in human.

2. An immunogenic polypeptide comprising a human IgE CH3 domain located between two non-placental mammalian IgE domains, wherein said immunogenic polypeptide is effective to induce an anti-human IgE response in a human, wherein the sequence of said immunogenic polypeptide is as set forth in SEQ ID NO:8.

3. An immunogenic polypeptide consisting of a human IgE CH3 domain, an opossum IgE CH2 domain, and an opossum IgE CH4 domain, wherein said human IgE CH3 domain is located between said opossum IgE CH2 domain and said opossum IgE CH4 domain.

* * * * *

UNITED STATES PATENT AND TRADEMARK OFFICE
CERTIFICATE OF CORRECTION

PATENT NO. : 6,913,749 B2
DATED : July 5, 2005
INVENTOR(S) : Dr. Lars T. Hellman It is certified that error appears in the above-identified patent and that said Letters Patent is hereby corrected as shown below:

Column 41,
Line 34, after "in" insert -- a --.

Signed and Sealed this

Seventh Day of March, 2006

JON W. DUDAS
*Director of the United States Patent and Trademark Office*